US010624543B2

(12) United States Patent
Zheng et al.

(10) Patent No.: US 10,624,543 B2
(45) Date of Patent: Apr. 21, 2020

(54) PHOTO-ACOUSTIC SENSING APPARATUS AND METHODS OF OPERATION THEREOF

(71) Applicant: Nanyang Technological University, Singapore (SG)

(72) Inventors: Yuanjin Zheng, Singapore (SG); Xiaohua Feng, Singapore (SG); Fei Gao, Singapore (SG)

(73) Assignee: Nanyang Technological University, Singapore (SG)

( * ) Notice: Subject to any disclaimer, the term of this patent is extended or adjusted under 35 U.S.C. 154(b) by 196 days.

(21) Appl. No.: 15/553,861

(22) PCT Filed: Mar. 4, 2016

(86) PCT No.: PCT/SG2016/050103
§ 371 (c)(1),
(2) Date: Aug. 25, 2017

(87) PCT Pub. No.: WO2016/140625
PCT Pub. Date: Sep. 9, 2016

(65) Prior Publication Data
US 2018/0064346 A1 Mar. 8, 2018

(30) Foreign Application Priority Data
Mar. 4, 2015 (SG) .............................. 10201501667P

(51) Int. Cl.
*A61B 5/00* (2006.01)
*A61B 5/01* (2006.01)
(Continued)

(52) U.S. Cl.
CPC .............. *A61B 5/0095* (2013.01); *A61B 5/01* (2013.01); *A61B 5/1477* (2013.01);
(Continued)

(58) Field of Classification Search
CPC ......... A61B 5/0095; A61B 5/01; A61B 5/024; A61B 5/7278; A61B 5/1477;
(Continued)

(56) References Cited

U.S. PATENT DOCUMENTS

| 5,085,080 A | 2/1992 | Yu |
| 6,049,728 A | 4/2000 | Chou |

(Continued)

FOREIGN PATENT DOCUMENTS

| CN | 1937956 A | 3/2007 |
| CN | 101043844 A | 9/2007 |

(Continued)

OTHER PUBLICATIONS

L. V. Wang, "Multiscale photoacoustic microscopy and computed tomography," Nat Photonics, vol. 3, pp. 503-509, Aug. 29, 2009.
(Continued)

*Primary Examiner* — Eric F Winakur
*Assistant Examiner* — Chu Chuan Liu
(74) *Attorney, Agent, or Firm* — Kilpatrick Townsend & Stockton LLP

(57) ABSTRACT

A photo-acoustic sensing apparatus (100) for non-invasive measurement of blood parameters of a subject (102) comprises a photo-acoustic sensor (104) for sensing photo-acoustic signals (106) induced when a region of the subject is illuminated by a light source (108). A first sensor processing module (112) may derive blood oxygen saturation using sensed photo-acoustic signals (114). A second sensor processing module (116) may derive blood core temperature using sensed photo-acoustic signals. A third sensor processing module (118) may derive blood glucose using sensed photo-acoustic signals. The sensing apparatus is configured to derive at least one of: a de-correlated value (120) of blood oxygen saturation of the subject; a de-correlated value (122)

(Continued)

of blood core temperature of the subject; and a de-correlated value (124) of blood glucose of the subject.

12 Claims, 8 Drawing Sheets

(51) Int. Cl.
 *A61B 5/145* (2006.01)
 *A61B 5/1477* (2006.01)
(52) U.S. Cl.
 CPC ...... *A61B 5/14532* (2013.01); *A61B 5/14542* (2013.01); *A61B 5/7278* (2013.01)
(58) Field of Classification Search
 CPC .............. A61B 5/1455; A61B 5/14551; A61B 5/14532; A61B 5/14542
 See application file for complete search history.

(56) References Cited

U.S. PATENT DOCUMENTS

| | | | |
|---|---|---|---|
| 6,070,093 A * | 5/2000 | Oosta | A61B 5/0095 356/39 |
| 6,405,069 B1 | 6/2002 | Oraevsky et al. | |
| 7,515,948 B1 | 4/2009 | Balberg et al. | |
| 7,717,948 B2 | 5/2010 | Demarais et al. | |
| 8,326,388 B2 | 12/2012 | Kanayama et al. | |
| 8,406,847 B2 | 3/2013 | Igarashi | |
| 2005/0054907 A1 | 3/2005 | Page et al. | |
| 2007/0015992 A1 | 1/2007 | Filkins et al. | |
| 2007/0197886 A1 | 8/2007 | Naganuma et al. | |
| 2009/0312628 A1 | 12/2009 | Igarashi | |
| 2012/0271204 A1 | 10/2012 | Peyman | |
| 2013/0035570 A1* | 2/2013 | Miyasato | A61B 5/0095 600/323 |
| 2013/0286379 A1 | 10/2013 | Li et al. | |
| 2014/0206960 A1 | 7/2014 | Nagae | |

FOREIGN PATENT DOCUMENTS

| | | |
|---|---|---|
| CN | 102908164 A | 2/2013 |
| CN | 103732154 A | 4/2014 |

OTHER PUBLICATIONS

L. V. Wang and S. Hu, "Photoacoustic tomography: in vivo imaging from organelles to organs," *Science*, vol. 335, pp. 1458-1462, Mar. 23, 2012.
X. Wang, Y. Pang, G. Ku, X. Xie, G. Stoica, and L. V. Wang, "Noninvasive laser-induced photoacoustic tomography for structural and functional in vivo imaging of the brain," *Nat Biotechnol*, vol. 21, pp. 803-806, Jul. 2003.
R. M. Schell and D. J. Cole, "Cerebral monitoring: Jugular venous oximetry," *Anesthesia and Analgesia*, vol. 90, pp. 559-566, Mar. 2000.
R. V. Kuranov, J. Z. Qiu, A. B. McElroy, A. Estrada, A. Salvaggio, J. Kiel, et al., "Depth-resolved blood oxygen saturation measurement by dual-wavelength photothermal (DWP) optical coherence tomography," *Biomedical Optics Express*, vol. 2, pp. 491-504, Mar. 1, 2011.
L. Gao, L. Wang, C. Li, Y. Liu, H. Ke, C. Zhang, et al., "Single-cell photoacoustic thermometry," *J Biomed Opt*, vol. 18, p. 26003, Feb. 2013.
J. Shah, S. Park, S. Aglyamov, T. Larson, L. Ma, K. Sokolov, et al., "Photoacoustic imaging and temperature measurement for photothermal cancer therapy," *J Biomed Opt*, vol. 13, p. 034024, May-Jun. 2008.
M. Pramanik and L. V. Wang, "Thermoacoustic and photoacoustic sensing of temperature," *J Biomed Opt*, vol. 14, p. 054024, Sep.-Oct. 2009.
S. H. Wang, C. W. Wei, S. H. Jee, and P. C. Li, "Photoacoustic temperature measurements for monitoring of thermal therapy," *Photons Plus Ultrasound: Imaging and Sensing 2009*, vol. 7177, 2009.
P. Zhang, X. Z. Zhang, J. Brown, D. Vistisen, R. Sicree, J. Shaw, et al., "Global healthcare expenditure on diabetes for 2010 and 2030," *Diabetes Research and Clinical Practice*, vol. 87, pp. 293-301, Mar 2010.
J. T. Oh, M. L. Li, H. F. Zhang, K. Maslov, G. Stoica, and L. H. V. Wang, "Three-dimensional imaging of skin melanoma in vivo by dual-wavelength photoacoustic microscopy," *Journal of Biomedical Optics*, vol. 11, May-Jun. 2006.
M. A. Pleitez, T. Lieblein, A. Bauer, O. Hertzberg, H. von Lilienfeld-Toal, and W. Mantele, "In Vivo Noninvasive Monitoring of Glucose Concentration in Human Epidermis by Mid-Infrared Pulsed Photoacoustic Spectroscopy," *Analytical Chemistry*, vol. 85, pp. 1013-1020, Jan. 15, 2013.
C. W. Freudiger, W. Min, B. G. Saar, S. Lu, G. R. Haltom, C. W. He, et al., "Label-Free Biomedical Imaging with High Sensitivity by Stimulated Raman Scattering Microscopy," *Science*, vol. 322, pp. 1857-1861, Dec. 19, 2008.
D. L. Liu and E. S. Ebbini, "Real-Time 2-D Temperature Imaging Using Ultrasound," *IEEE Transactions on Biomedical Engineering*, vol. 57, pp. 12-16, Jan. 2010.
M. Pernot, M. Tanter, J. Bercoff, K. R. Waters, and M. Fink, "Temperature estimation using ultrasonic spatial compound imaging," *IEEE Transactions on Ultrasonics Ferroelectrics and Frequency Control*, vol. 51, pp. 606-615, May 2004.
L. R. Hirsch, R. J. Stafford, J. A. Bankson, S. R. Sershen, B. Rivera, R. E. Price, et al., "Nanoshell-mediated near-infrared thermal therapy of tumors under magnetic resonance guidance," *Proceedings of the National Academy of Sciences of the United States of America*, vol. 100, pp. 13549-13554, Nov. 11, 2003.
B. Quesson, J. A. de Zwart, and C. T. W. Moonen, "Magnetic resonance temperature imaging for guidance of thermotherapy," *Journal of Magnetic Resonance Imaging*, vol. 12, pp. 525-533, Oct. 2000.
H. F. Zhang, K. Maslov, M. Sivaramakrishnan, G. Stoica, and L. H. V. Wang, "Imaging of hemoglobin oxygen saturation variations in single vessels in vivo using photoacoustic microscopy," *Applied Physics Letters*, vol. 90, Jan. 29, 2007.
J. K. Chen, M. L. Wang, J. C. Cheng, Y. H. Wang, P. C. Li, and X. Y. Cheng, "A Photoacoustic Imager With Light Illumination Through an Infrared-Transparent Silicon CMUT Array," *IEEE Transactions on Ultrasonics Ferroelectrics and Frequency Control*, vol. 59, pp. 766-775, Apr. 2012.
International Search Report corresponding to PCT/SG2016/050103, dated Jun. 13, 2016, three pages.
International Preliminary Report on Patentability corresponding to PCT/SG2016/050103, dated Sep. 5, 2017.
Office Action dated Dec. 31, 2019 in Chinese Patent Application No. 2016800136598, filed Mar. 4, 2016, 36 pages.
Xia, J., et al. "Photoacoustic tomography: principles and advances." Electromagnetic waves (Cambridge, Mass.), vol. 147: 1-22, DOI:10.2528/pier14032303, 2014, 31 pages.

* cited by examiner

Absorption spectrum of glucose

PHOTO-ACOUSTIC SENSING APPARATUS AND METHODS OF OPERATION THEREOF

The invention relates to a photo-acoustic sensing apparatus for non-invasive measurement of blood parameters of a subject. The invention may also relate to deriving a de-correlated value of blood oxygen saturation of the subject. The invention may also relate to deriving a de-correlated value of blood core temperature of the subject. The invention may also relate to deriving a de-correlated value of blood glucose of the subject. The invention also relates to corresponding methods.

The photo-acoustic (PA) effect refers to acoustic wave generation of a material via thermoelastic mechanism when illuminated by, for example, intensity modulated light. It is a fast-growing multi-wave technique with increasingly more applications in biomedical sensing owing to its unique capacity in high resolution probing of rich optical contrast in vivo at depths (down to several centimetres) [1]. As blood offers primary contrast in photo-acoustic techniques, it is particularly suited for imaging the vasculature and measuring other physiological parameters (e.g. haemoglobin, oxygen, sodium) therein. Moreover, with light being the only electromagnetic wave that is sensitive to molecular conformation, it has the versatility in probing anatomical, functional, metabolic, molecular, and genetic contrasts of vasculature, hemodynamics, oxygen metabolism, biomarkers, gene expression, etc. The flexibility in tailoring the photonic and ultrasonic parameters allows it to be customised in vastly different applications with scales varying from organelles to organs and penetration depth from superficial layers of several millimetres to an aggressive depth of 7 centimetres [2]. In fact, various uses of the photo-acoustic effect have been demonstrated. On the small end of the scale, a compact functional photo-acoustic microscopy (fPAM) system is developed (such as an endoscopic probe), which pertains an imaging resolution down to 15 µm and a penetration depth more than 3 mm. On the large end of the scale, a photo-acoustic tomography system is built by which the whole brain of a rat is imaged noninvasively in vivo with the skin and skull intact [3]. Besides its scalability, the application frontiers for photo-acoustic techniques are expanding in a number of areas.

Non-Invasive Oxygen Saturation Monitoring

Oxygen saturation (SO2) is considered an important physiological parameter of human health and disease, and holds promise as a tool in this regard. The SO2 of blood in the arteries (SaO2) reflects the adequacy of oxygen supply, and SO2 of blood returning from the organs in the veins (SvO2) to the right side of the heart (also called central venous oxygen saturation) reflects the consumption of oxygen by the organs.

Currently, measuring central venous SvO2 is not easy; it requires the use of invasive central venous catheters (CVC) inserted from the internal jugular vein into the right atrium of the heart. Some CVCs are equipped with oxymetric infrared probes that can measure the SvO2 in real-time and have been used to monitor cerebral [4] or central venous SO2. However, the insertion of CVCs is not without risks, and may not be justified if only to be used to detect the patients in early shock.

Current non-invasive technologies, such as near-infrared spectroscopy (NIRS) are limited by insufficient sensitivity, volume-averaged inaccuracy due to strong optical scattering and diffusing, and poor penetration depth and cannot measure the SvO2 in the right atrium. Other techniques such as blood-oxygen-level-dependent (BOLD) contrast MRI, electron paramagnetic resonance imaging (EPRI), spectroscopic optical coherence tomography (SOCT) [5], PET and SPET are expensive, cumbersome and illsuited to these purposes.

In the literature, US20070015992A1 [14], US840684762 [15] and US751594861 [16] implement photo-acoustic-based SO2 measurements.

Non-Invasive Blood Core Temperature Measurement

Real time non-invasive body core temperature measurement has been pursued for a long time, with only limited success. The demand for such a device is huge and its realisation is not trivial. Convenient and reliable temperature monitoring during physical activities, in particular, needs to be made on a non-invasive continuous basis and therefore portable sensors are necessary which further implicates lightweight and low power consumption for the device. These additional constraints result in even less options when considering possible solutions.

Recently, tissue temperature monitoring by photo-acoustic technology has been proposed due to its high sensitivity. The reported temperature measurements vary in accuracy and resolution, depending on the applications. As reported in [6], the temperature in a single cell is measured with accuracy of 0.2 degrees Celsius and in [7], temperature for cancer therapy is monitored with an accuracy of 0.16 degrees Celsius without accounting the laser energy fluctuations. As reported in [8], an improved temperature sensitivity of 0.15 degrees Celsius obtained in a 2 seconds temporal resolution and 0.015 degrees Celsius when temporal resolution is scaled to 200 seconds. Therefore, the measurement accuracy is highly scalable based on the desired measurement resolution. However, it should be pointed out that all those reported temperature measurements are carried out on tissue-mimicking phantoms or ex vivo excised tissues. No in vivo absolute temperature measurements at depths have been demonstrated yet, though it is observed in some in vivo experiments [9] that measured photo-acoustic signals show a strong dependence on temperature.

A method of measuring the temperature of a sample or its surrounding pressure is proposed in U.S. Pat. No. 5,085,080, using the fundamental photo-acoustic effect to measure the resonant frequency of the sample. Only the temperature changes can be measured at the sample surface according to the original method [24].

Non-Invasive Glucose Monitoring

Diabetes is a prevalent chronic disease with very high levels of medical and economic burden. It was reported to afflict 347 million people worldwide in 2010 and estimated to reach 366 million in 2030, which is 4.4% of the world population. This is especially significant in aging populations, such as in Singapore. Diabetes causes multiple chronic severe systemic complications. It also results in multiple skin diseases, including bacterial and fungal infections, generalised itch, diabetic dermopathy, necrobiosis lipoidica diabeticorum, diabetic blisters, and eruptive xanthomatosis etc. To decrease the impact of diabetes on patients' health, regular monitoring and control of blood glucose level is of utmost importance. Currently, finger-prick devices are used for monitoring but they cause pain and may result in complications such as infections due to its invasion, and the cumulative cost of using the strips is high. A non-invasive device that can be used to repeatedly measure glucose level (easy to measure at a certain skin layer and it is proportional to the blood glucose level) will therefore present as a technological feat. Such a device will potentially improve the quality of life of patients significantly and greatly reduce the medical, social and economic burden of the disease [10].

A plethora of attempts had been devoted to the development of non-invasive devices using different technologies. Yet limited success has been met and none of those devices were fully successfully commercialised. Some devices were able to obtain FDA approval but were subsequently withdrawn several years later. Others are either still trying to obtain approval or under further improvements before becoming fully applicable in practical settings. Owing to the rich optical contrasts of tissues and non-ionisation nature of light, most of the non-invasive technologies are optical methods with a few other exceptions being impedance spectroscopy and electromagnetic sensing [11]. In near-infrared spectroscopy, glucose concentration is calculated from the light transmission spectrum and with multivariate techniques; it even allows glucose level measurement inside complex biological matrices. Unfortunately, it is susceptible to noise and interference from other light absorbing components (water, haemoglobin etc), which reduces the measurement accuracy significantly. Mid-infrared spectroscopy (MIR) utilises light with wavelengths in the range 2500-10000 nm for sensing but the penetration is severely limited at several micrometres due to the strong water absorption at this range [12]. Additionally, the MIR spectrum is highly sensitive to tissue hydration. Raman spectroscopy is capable of label-free and molecule specific detection in a highly specific manner [13].

However, besides the instability of laser, interferences from other compounds persisted as different molecules may show similar absorbing spectrum. Impedance spectroscopy relies on measuring tissue impedance over a frequency range to extrapolate glucose concentration. Unfortunately, with many factors such as diseases that affect the cell membranes can also change the dielectric properties significantly, the specificity of this method is poor.

The invention is defined in the independent claims. Some optional features of the invention are defined in the dependent claims.

Implementation of the techniques disclosed herein may provide significant technical benefits. For instance, provision of a sensing apparatus having sensing components for measurement of oxygen saturation, blood core temperature and blood glucose in a subject realises hitherto unobtained convenience by having the sensing components for performing three different types of measurement in a single device. Indeed, the sensing apparatus may be provided with an integral sensor head incorporating the components for measurement of all three parameters. In at least one arrangement, the proposed photo-acoustic sensor solution can concurrently measure multiple core parameters (blood SO2, core temperature, glucose), making the solution much more cost effective and robust than existing commercial products Further, implementation of the described techniques for the derivation of a de-correlated value of blood oxygen saturation of the subject provides a significant technical benefit in that, the derived value is unaffected by variations in blood temperature and blood glucose levels.

Known blood oxygen saturation detection using optical techniques have needed at least two wavelengths to differentiate between oxygenated haemoglobin and deoxygenated haemoglobin for the SO2 calculation. As described herein, it is possible to use a scattered optical signal and a photo-acoustic signal, where the optical source emits light of a single wavelength only, to extract the blood oxygen saturation information. Clearly, this leads to a significantly lower capital cost in the light source, overall reduced system complexity and may particularly lend itself for use in continuous monitoring of blood oxygen saturation.

Yet further, implementation of the described techniques for the derivation of a de-correlated value of blood core temperature of the subject provides a significant technical benefit in that, the derived value is unaffected by variations in blood oxygen saturation and blood glucose levels. The techniques described herein may allow quantitative measurement of the absolute temperature in the blood and tissue non-invasively.

Moreover, implementation of the described techniques for the derivation of a de-correlated value of blood glucose of the subject provides a significant technical benefit in that, the derived value is unaffected by variations in blood oxygen saturation and blood temperature.

The photo-acoustic guided transmission method as described herein may emulate a virtual photodiode inside the tissue (where the glucose is to be measured) to monitor the transmitted light. Due to the reduced propagation thickness and the scalable size for the virtual photodiode, the sensing resolution may be improved. And more importantly, if the photo-acoustic waves that possess inherent high signal-to-noise ratio are sensed rather than light detection, this method may have better signal to noise ratio and may be more resilient to environmental light interference that is suffered by NIRS. Furthermore, the photo-acoustic guided transmission method is more immune to strong haemoglobin interferences if it enables a sensing region that avoids blood vessels. With multiple wavelengths to isolate the abundant water, protein and fat inside the skin layer, the achieved photo-acoustic guided transmission method may be capable of sensing with much better specificity.

The photo-acoustic guided transmission method may use a normalisation procedure to account for the "guide star" (virtual photodiode) fluctuation caused by human metabolism. Such normalisation may also rectify the temperature effect on glucose measurement, eliminating a major interference factor in conventional methods like NIRS. Furthermore, when integrating glucose measurement and core temperature measurement, even second order temperature effects on the measurement accuracy and robustness can be corrected.

As the photo-acoustic signal generated by laser diodes (when used as the light source) is inherently limited compared to the bulky solutions, highly sensitive signal detection and processing may provide high quality measurement. Through co-design between the photo-acoustic cell, the photo-acoustic sensor (e.g. the microphone) and low noise amplifier (LNA) and by adopting coherent detection, accurate signal detection is potentially attainable.

Advantages of the techniques described herein over known techniques are now discussed.

Blood Oxygen Saturation Sensing

A comparison is shown in Table 1 below in terms of methodology, safety, complexity, sensitivity, localisation and so on.

TABLE 1

Benchmarking of different technologies for non-invasive SO2 monitoring

| Parameter | SO2 catheter (Gold standard) | Available Pulse oximeter | Perfusion MRI | Disclosed PA oximeter |
|---|---|---|---|---|
| Methodology | NIR spectroscopy | NIR spectroscopy | Contrast agent | Photoacoustics |
| Specificity | High | Low: limited wavelength and optical scattering | Low: need external agent | High: bond-selective vibration PA |
| Sensitivity | High (<0.1%) | Low: strong optical scattering and volumetric detection | Medium | High (<0.1%): sensitive acoustic detection |
| Reliability | High | Low: single optical wave measurement | Low: no absolute SO2 value | High: Multi-parameter fusing and correlation |
| Penetration | Good: Insertion | Poor: strong scattering | Good: magnetic field | Good: acoustic penetration |
| Localization | Good (<1 mm) | Bad (<1 mm) due to strong scattering | Good: MRI resolution | Good (<1 mm) due to acoustic focusing |
| Risk | High: invasive | Low: non-invasive | Medium: strong magnetic field | Low: non-invasive |
| Cost | High: complexity and invasive | Low: laser diode and detector | High: expensive MRI machine, operation cost | Low: single-wavelength laser; integrated acoustic sensor |
| Real-time | No | Yes | No | Yes |

The underlying principle of the disclosed photo-acoustic oximeter (blood oxygen saturation meter) is based on the photo-acoustic phenomenon, transmitting light and receiving ultrasound. A light source, such as a laser module, may be included or provided separately to generate single- and/or multi-wavelength light, a photo-acoustic sensor such as an ultrasound transducer array may be provided to receive the induced photo-acoustic signals and transfer/convert these to electrical signals, and electrical control module to process the signals (for example, amplification, filtering and digitizing) may be provided for blood oxygen saturation extraction. Due to the specific optical absorption properties of deoxygenated haemoglobin (HbR) and oxygenated haemoglobin (HbO2) within the near infrared (NIR) range (when the light source emits light in this part of the spectrum), photo-acoustic signals generated from the optical absorption of HbR and HbO2 in the blood will be related to the ratio between HbR and HbO2. Single-wavelength and multi-wavelength light illumination can be performed for SO2 extraction reliably based on proposed phasoscopy approach and multi-parameters fusion. Due to the deep penetration of NIR light (>2 cm), when used, optical absorption of, for example, the carotid and jugular blood inside the human neck will induce sufficiently strong photo-acoustic signals, which may be detected by a photo-acoustic sensor such as an ultrasound transducer. Thanks to the reduced scattering of acoustic waves when compared to that of photons, the induced photo-acoustic signals may maintain their pulse waveforms and render the accurate localisation of the targeted vessels. Therefore, the SO2 extracted from the photo-acoustic and scattered light signals may be used to deliver one or more of continuous monitoring, high sensitivity, localisation and penetration.

In the prior art documents US20070015992A1 [14], US840684762 [15] and US751594861 [16] mentioned above, each of these implements photo-acoustic-based SO2 measurements utilising at least two wavelengths.

Blood Core Temperature Sensing

Non-invasive temperature measurement generally depends on applying different kinds of waves that can penetrate into a material to probe, either directly or indirectly, certain physical parameters. Various waves have been used, including mechanical waves like ultrasound, electromagnetic waves like radio frequency and light waves, and even thermal waves as well, each with their own strengths and limitations. Being portable and low cost, diagnostic ultrasound-based methods [17, 18] can penetrate deep into human body and provide real time temperature information. However, the accuracy of this method is not good due to its weak sensitivity to temperature. Magnetic resonance thermometry [19, 20] is currently the gold standard in guiding high intensity focused ultrasound therapy owing to its excellent accuracy and good spatial resolution. Unfortunately, it is only suitable for scenarios where the temperature variation is relatively slow and therefore cannot be real time. Apart from additional hindrances imposed by motion artefacts due to breathing and movements, its primary limitations are high cost and large size, which prevent its usage in portable applications. Infrared thermography [21] allows for temperature monitoring in real time with accuracy better than 0.1 Celsius but it can only sense the temperature at the surface of an object (<0.5 mm), not to mention its inability to extract physiological parameters for functional diagnosis of the probed region. Known pure optical methods [22, 23] are sensitive to tissue physiological parameters including temperature, and thus are potential for its monitoring. However, the strong scattering of light within tissue precludes it from achieving high resolution monitoring of temperature at depth, for instance, in the carotid or pulmonary artery. Indeed, initial successful demonstrations of PA based temperature measurement have already been achieved although further engineering work has to be done to make it suitable for human core temperature measurement. Furthermore, to better monitor heat strain, additional physiological parameters may also be measured to provide more concrete information for monitoring and to decouple their effects on temperature measurement since physiological parameters in vivo usually show intricate inter-dependences. This can be done relatively easily, as compared with other mentioned technologies, with spectroscopic PA techniques by choosing appropriate wavelengths of laser light for the probing.

Benchmarked in Table 2, the advantage and potential of the proposed PA sensing technique are clearly demonstrated as its system complexity, power consumption and accuracy can be tailored to meet the requirements for the targeted applications.

Glucose Sensing

Known methods are constrained to single wave sensing, leaving them with less headroom for technological modification and improvement. Photo-acoustic sensing techniques [2, 25], on the other hand, may combine the advantages of two waves: the rich contrast, high sensitivity of optical wave and extra benefits offered by, for example, ultrasound technology, depth profiling for instance. It may provide versatile functional sensing capability and outstanding system scalability. Moreover, the advantages of the optical method are generally well incorporated in photo-acoustic techniques. Photo-acoustic sensing suffers less interference from water, the ubiquitous substance in all tissues, as water exhibits relatively poor photo-acoustic response. Interferences from other compounds though persistent, can be reduced significantly by adopting photo-acoustic spectroscopy techniques.

TABLE 1

Benchmarking of available technologies for non-invasive temperature monitoring

| Parameter | Ultrasound | Magnetic resonance thermometry | Infrared thermometry | Pure optical methods | Disclosed PA sensor |
|---|---|---|---|---|---|
| Penetration | Good | Good | Poor, only superficial | Poor | Medium to High |
| Sensitivity | Medium | High | High | High | High |
| Accuracy | 0.2 Degree | 0.1 Degree | 0.1 Degree | 0.1 Degree | Scalable, 0.1 Degree |
| System Complexity | Medium | High | Low | Medium | Medium |
| Power Consumption | Low | High | Low | Low | Low to Medium Scalable |
| Real Time | Yes | No | Yes | Yes | Yes |
| Functional Measurement | Limited | Good | Severely limited | Excellent | Excellent |

In comparison with the prior art documents mentioned earlier, the techniques disclosed herein may allow quantitative measurement of the absolute temperature in the tissue non-invasively. This may be realised through an "active perturbation" method that may utilise an innovative laser firing sequence without necessary calibration and interference from other physiological parameters such as haemoglobin concentration.

Lastly, the proposed PA guided transmission method is inherently immune to temperature fluctuations, a major interference factor for pure optical methods [25]. The different technologies currently available for non-invasive monitoring are presented in Table 3. The advantage and potential of the proposed photo-acoustic sensing technique are clearly demonstrated, and its measurement specificity, accuracy and device size can be tailored to meet the requirements of different applications.

TABLE 3

Benchmarking of different technologies for non-invasive glucose monitoring

| Parameter | Near-infrared Spectroscopy | Mid-infrared Spectroscopy | Raman Spectroscopy | Impedance Spectroscopy | Disclosed PA Spectroscopy |
|---|---|---|---|---|---|
| Depth Profiling | No | No | No | No | Yes |
| Penetration | >1 mm | Several μm | Limited | Large | >1 mm scalable |
| Measurement Site | Finger, forearm skin, ear | Finger skin, oral mucosa | Eye, skin (large error) | Wrist | Skin, arms, finger, forehead, etc |
| Major Interfering Factors | Water, fat, proteins, haemoglobin temperature etc. | Water, fat, proteins, haemoglobin, temperature, etc. | Lipids | Water, diseases that affect cell membranes | Lipids, melanin |
| Specificity | Good | Good | Good | Poor | Excellent |
| Size | Large | Large | Large | Portable | Scalable |

In the literature patents, photo-acoustic based methods for glucose detection and measurement have been proposed. US6049728A presents a photo-acoustic method for blood glucose measurement [26] which is not suitable for targeting deep tissue in vivo because of its limited sensitivity and selectivity. US6405069B1 applies a photo-acoustic technique to monitor glucose concentration in the eye tissue [27]. U.S. Pat. No. 8,326,388B2 [28] and US20120271204 [29] develop the basic photo-acoustic concept for measuring body glucose. Furthermore, a portable and wearable glucose measurement system such as an implementation in a wristwatch is proposed [30]. However, all the methods mentioned above for glucose measurement are in an elementary photo-acoustic configuration, and have not gained at sensitivity and selectivity. The photo-acoustic guided transmission spectroscopy techniques disclosed herein are different from existing techniques. They may be considered to introduce a virtual photodiode inside tissue which may enable sensing glucose with better resolution and higher specificity. In addition, the disclosed sensor may be configured so that it may concurrently measure SO2 and temperature, and thus it is able to de-embed the interference from glucose measurement, making it more robust and accurate.

In summary, the advantages of the disclosed techniques may be able to achieve are:

Higher Specificity

The photo-acoustic guided transmission method is more immune to strong haemoglobin interference as it enables a sensing region that avoids blood vessels. Meanwhile, with multiple wavelengths to isolate the abundant water, protein and fat inside the skin layer, the achieved photo-acoustic guided transmission light transmission spectroscopy may be capable of sensing with much better specificity.

Higher Sensitivity

The photo-acoustic guided transmission method may emulate a virtual photodiode inside the tissue to monitor the transmitted light. Due to the reduced propagation thickness and the scalable size for the virtual photodiode, the sensing resolution may be improved. And more importantly, since the photo-acoustic waves that possess inherent high signal-to-noise ratio are sensed rather than light, this method may have better signal to noise ratio and may be resilient to environmental light interferences that are suffered in NIRS. Also, an advanced capacitive micro-machined ultrasonic transducer (CMUT), when utilised as the photo-acoustic sensor, may detect the photo-acoustic signal with higher sensitivity than a conventional piezoelectric transducer.

Higher Reliability

The photo-acoustic guided transmission method uses a normalisation procedure to account for the "guide star" (virtual photodiode) fluctuation caused by human metabolism. Such normalisation may also rectify the temperature effect on glucose measurement, eliminating a major interference factor in conventional methods like NIRS. Furthermore, by integrating glucose measurement and core temperature measurement, even second order temperature effects can be corrected.

Lower Cost

When implemented as single-wavelength SO2 detection, this may lower the light source (e.g. laser) system cost without decreasing the sensitivity significantly. The cost of, for example, a highly integrated CMUT array is drastically reduced taking advantage of standard semiconductor fabrication process.

The invention will now be described, by way of example only, and with reference to the accompanying drawings in which:

FIG. 4b is a graph illustrating the experimental results from the set up of FIG. 4a;

FIG. 7b is a graph illustrating the experimental results from the setup of FIG. 7a;

Figure 11:
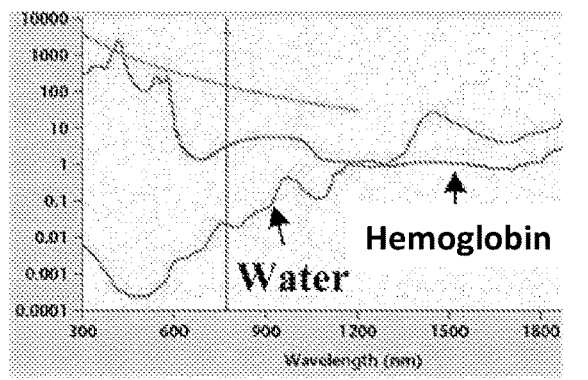
Figure 11:
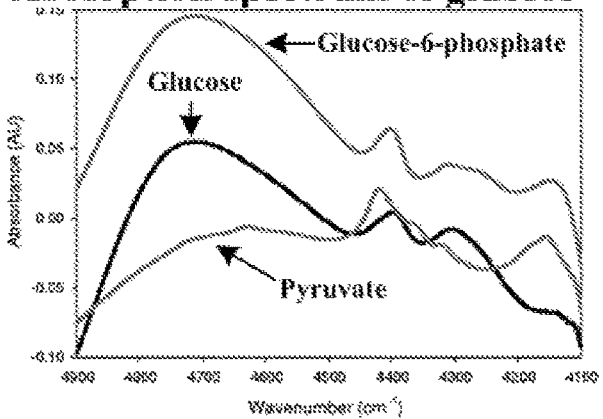
Figure 12:
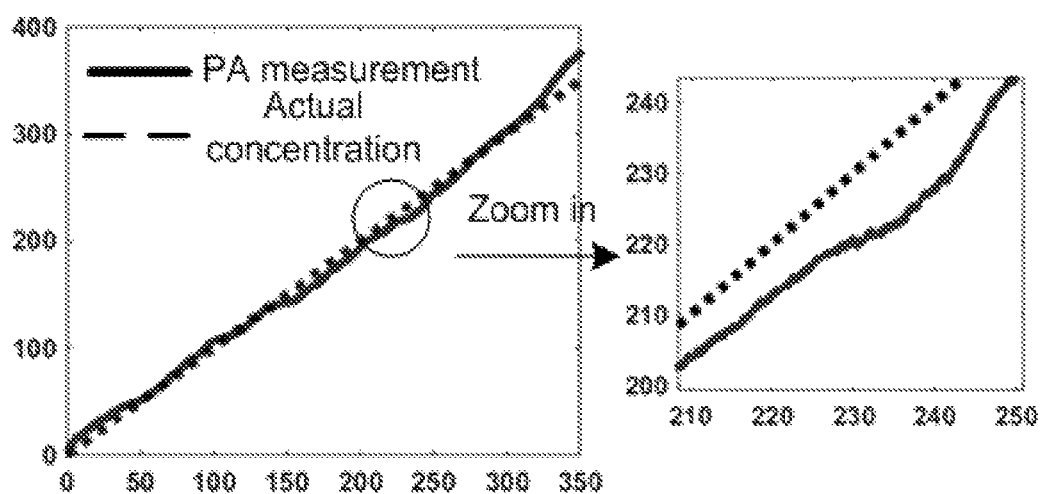

FIG. 11 provides a pair of graphs illustrating the absorption spectrum of glucose, water and haemoglobin; and FIG. 12 provides a graph illustrating the glucose concentration measurement results and glucose detection.

Figure 1:
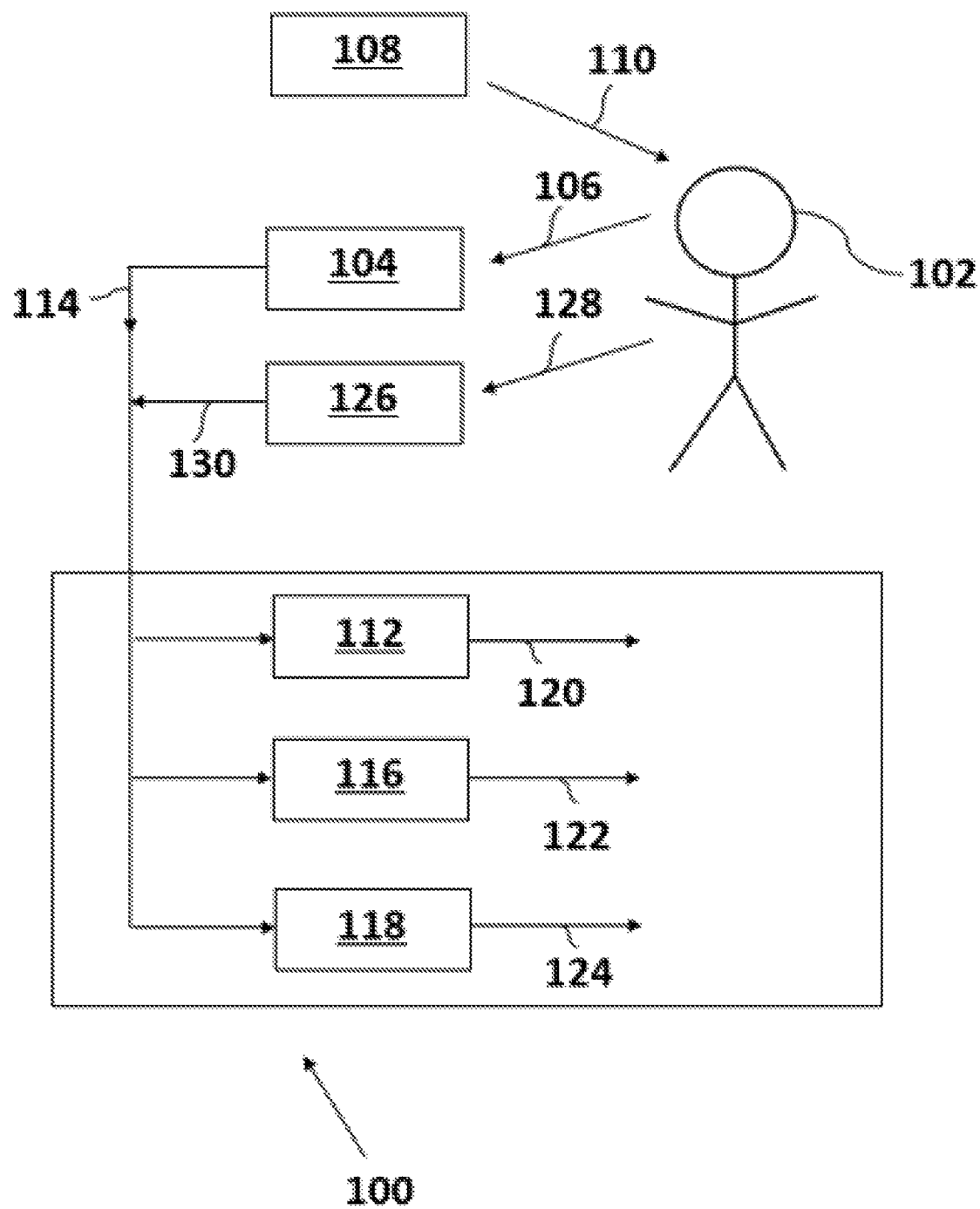
FIG. 1 is a block schematic diagram illustrating a photo-acoustic sensing apparatus for non-invasive measurement of blood parameters of a subject.

Turning first to FIG. 1, an exemplary photo-acoustic sensing apparatus 100 for non-invasive measurement of blood parameters of the subject 102 is illustrated. The photo-acoustic sensing apparatus 100 comprises a photo-acoustic sensor 104, a first sensor processing module 112, a second sensor processing module 116 and third sensor processing module 118. Photo-acoustic sensing apparatus 100 may optionally comprise a light source 108, or this may be provided separately.

Figure 3:
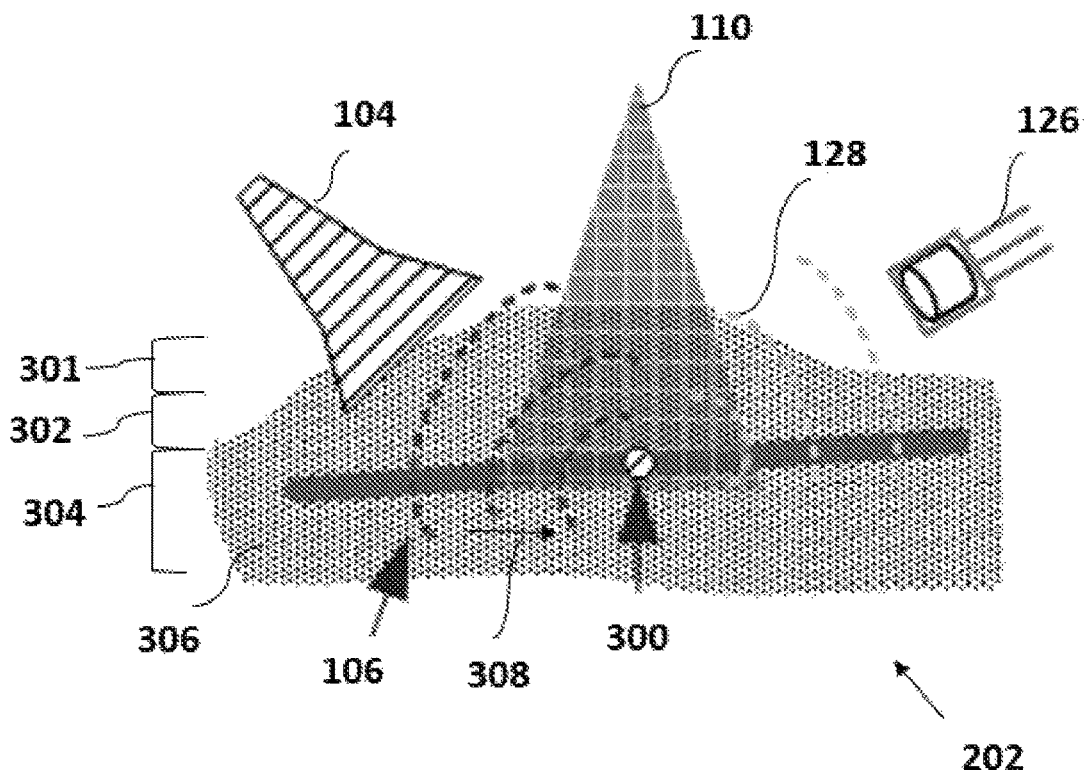
FIG. 3 is a schematic diagram illustrating an exemplary photo-acoustic technique for measuring blood oxygen saturation.
Figure 5:
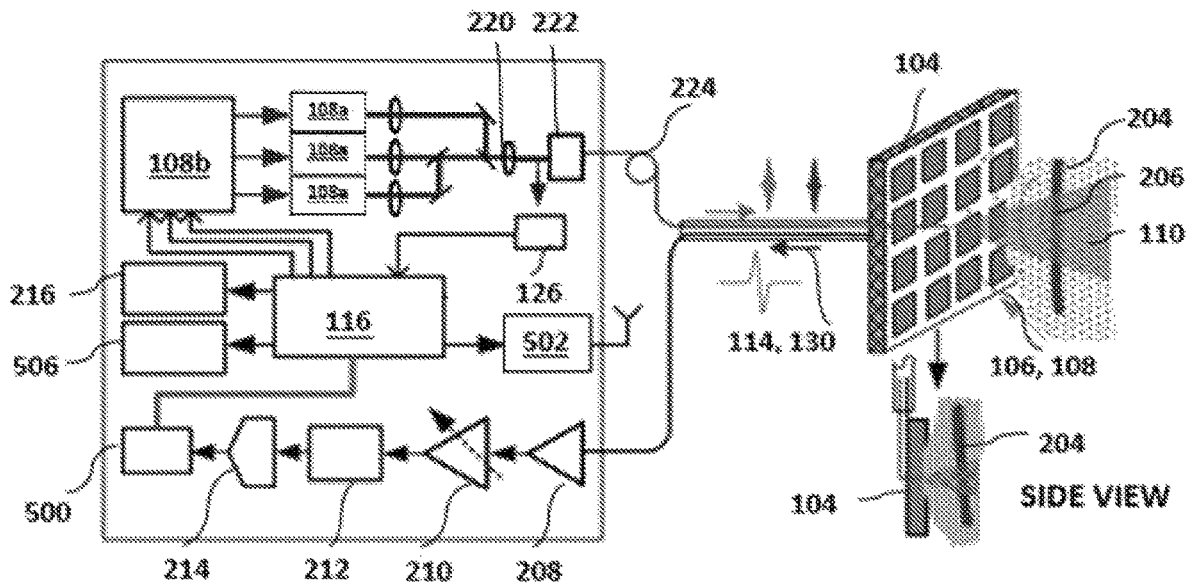
FIG. 5 is a schematic diagram illustrating an exemplary photo-acoustic technique for measuring blood core temperature.
Figure 8:
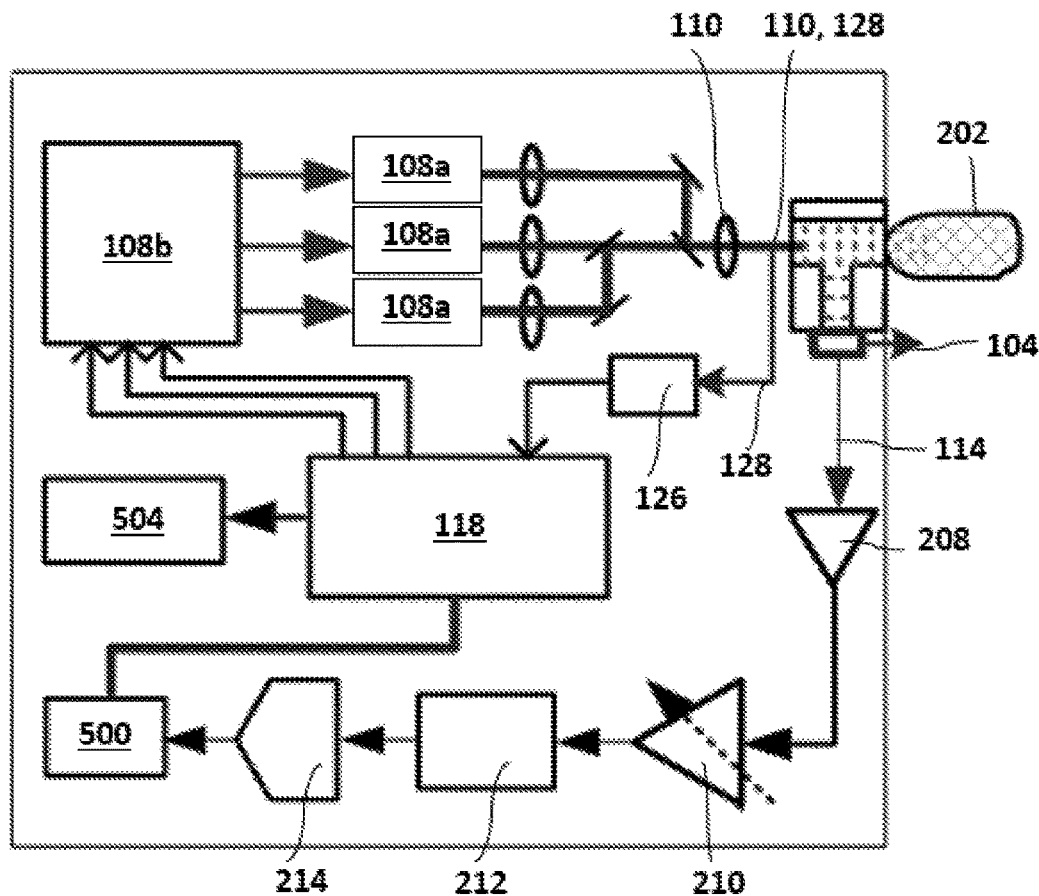
FIG. 8 is a schematic diagram illustrating an exemplary photo-acoustic technique for measuring blood glucose.

Light source 108, for example a laser such as a laser diode, is configured to emit light 110 towards subject 102 (or, rather, a target region of the subject, as will be shown in more detail in FIGS. 3, 5 and 8). Photo-acoustic sensor 104 picks up photo-acoustic signals (e.g. acoustic waves) 106 induced when the region of the subject 102 is illuminated by the light 110 from light source 108. Photo-acoustic sensor 104 outputs sensed photo-acoustic signals 114, for use by one or more of the first, second and third processing modules 112, 116, 118.

Photo-acoustic sensing apparatus 100 may also comprise a light sensor 126 which may be configured to measure scattering of light 128 scattered by the region of the subject 102, when illuminated by the light 110. For this detection, it is possible for light sensor 126 (such as one or more photodiodes) to be attached to the ultrasound transducer, facing the subject, allowing it to receive the backscattered light from the subject. Light sensor 126 outputs sensed scattered light signals 130 for use by the processing modules 112, 116, 118.

First sensor processing module 112 is configured to derive blood oxygen saturation using at least the sensed photo-acoustic signals 114, although the sensed scattered light signals 130 are advantageously used in the derivation.

Second sensor processing module 116 is configured to derive blood core temperature using at least the sensed photo-acoustic signals 114. Third sensor processing module 118 is configured to derive blood glucose using at least the sensed photo-acoustic signals 114, although the sensed scattered light signals 130 are advantageously used in the derivation.

As will be described in greater detail below, first sensor processing module 112 is able to derive a de-correlated value 120 of blood oxygen saturation of the subject. Second sensor processing module 116 is able to derive a de-correlated value 122 of blood core temperature of the subject. Third sensor processing module 118 is able to derive a de-correlated value 124 of blood glucose of the subject. Each of these de-correlated values 120, 122, 124 may be made available for analysis.

Thus, it will be appreciated that FIG. 1 illustrates a photo-acoustic sensing apparatus 100 for non-invasive measurement of blood parameters of a subject 102, the photo-acoustic sensing apparatus 100 comprising a photo-acoustic sensor 104 for sensing photo-acoustic signals 106 induced when a region of the subject 102 is illuminated by a light source 108. The first sensor processing module 112 is configured to derive blood oxygen saturation using sensed photo-acoustic signals 114. The second sensor processing module 116 is configured to derive blood core temperature using sensed photo-acoustic signals 114. Third sensor processing module 118 is configured to derive blood glucose using sensed photo-acoustic signals. The photo-acoustic sensing apparatus 100 is configured for at least one of: the first sensor processing module 112 to derive a de-correlated value 120 of blood oxygen saturation of the subject; the second sensor processing module 116 to derive a de-correlated value 122 of blood core temperature of the subject; and the third sensor processing module 118 to derive a de-correlated value 124 of blood glucose of the subject.

FIG. 1 also illustrates the photo-acoustic sensing apparatus 100 may comprise a light sensor 126 for sensing scattered light signals 128 induced when the region of the subject 102 is illuminated by the light source 110. Further, the first sensor processing module 112 is configured to derive the de-correlated value of blood oxygen saturation of the subject using the sensed photo-acoustic signals and sensed scattered light signals, the de-correlated value of blood oxygen saturation being related to a ratio of oxygenated haemoglobin in blood of the subject and total haemoglobin in the blood of the subject.

Blood Oxygen Saturation

Figure 2:
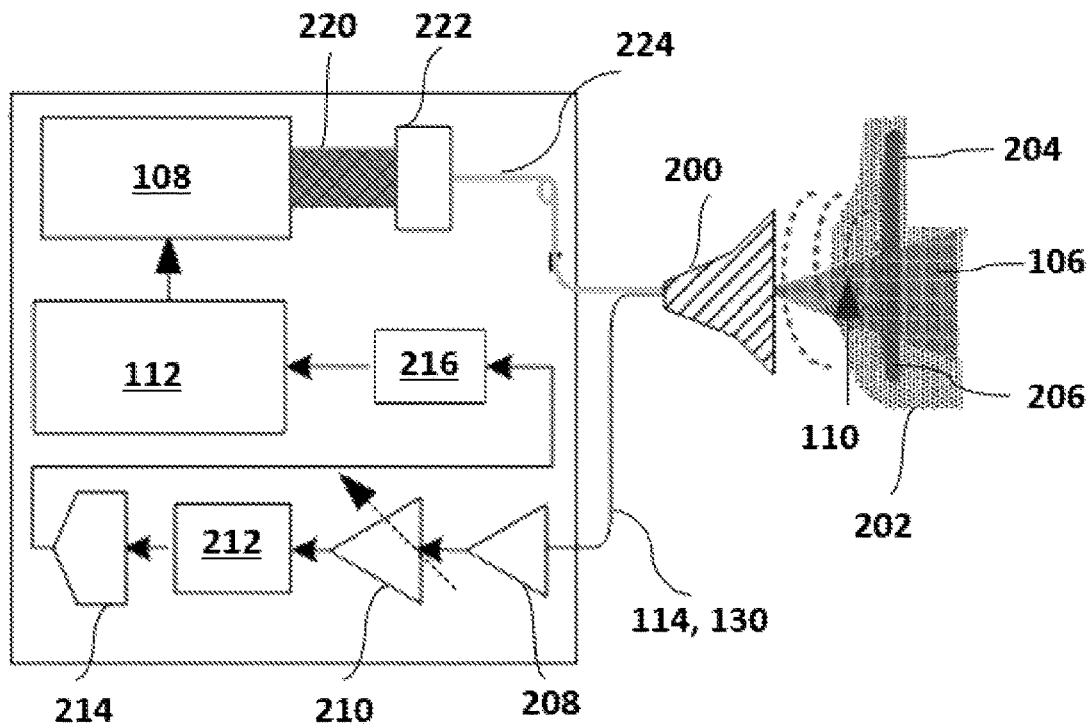
FIG. 2 is a schematic line diagram illustrating components of an exemplary sensor processing module for deriving blood oxygen saturation.

An exemplary architecture for a sensor processing module for deriving blood oxygen saturation is illustrated in FIG. 2. In this example, the sensor head 200 is an integrated sensor head incorporating the photo-acoustic sensor 104 and the light sensor 126. Integrated sensor head 200 is also configured to emit light 110 towards the target region 202 of the subject 102. It will be appreciated that, in other exemplary arrangements, separate sensor heads may be provided for the photo-acoustic sensor and the light sensor. Furthermore, a separate light emitter may also be provided.

In the example of FIG. 2, the light being emitted by integrated sensor 200 is laser light, and this is directed at region 202 in order to illuminate the blood vessel 204 of the subject, having blood 206 flowing therethrough. Sensed photo-acoustic signals 114 and sensed scattered light signals 130 are conveyed back to a low noise amplifier 208, and processed by a variable gain amplifier 210, a filter 212, analogue to digital converter 214 and DSP module 216 prior to being transmitted to first sensor processing module 112.

The derived de-correlated value of blood oxygen saturation may be made available, for example, for display on a display (not shown).

As mentioned above, in this example integrated sensor head 200 emits laser light. Thus, the apparatus further comprises a laser system 108 which emits a laser beam 220 to fibre coupler 222 which couples the laser light signal into fibre 224.

The exemplary sensor may be portable and comprises a non-invasive photo-acoustic blood oxygen saturation imaging sensor, which may be termed a photo-acoustic oximeter, based on the photo-acoustic phenomenon and technique, which may have particular application for continuous monitoring blood oxygen saturation with high sensitivity. This exemplary photo-acoustic oximeter mainly integrates the pulsed laser system, the ultrasound transducer array as the photo-acoustic sensor 104, and the signal processing modules mentioned above. During operation in, for example, clinics, this device may be attached or held adjacent to human skin with gel coupling with a view to the target region being a region around, for example, the carotid or jugular vessels. In some arrangements, this may enable continuous monitoring with high sensitivity (0.1%), reliability (e.g. when implementing multi-parameter correlation and calibration) and deep penetration (>2 cm). As will be described in more detail below, blood oxygen saturation may be extracted from the laser-induced photo-acoustic signal and scattered light signal using only single-wavelength light illumination.

The exemplary arrangement of FIG. 2 includes, as mentioned, a laser module capable of generating a multi-wavelength light source, which is coupled into a fibre such as a multimode fibre and delivered to illuminate human vessels. It also includes, for the photo-acoustic sensor 104, an ultrasound transducer array, which may be made of piezoelectric material or capacitive micro-machined ultrasound transducer (CMUT), to receive the induced photo-acoustic signals 106 and convert these to electrical signals 114. The light illumination and ultrasound transducer array may be aligned to be confocal to maximize the detection sensitivity. The optical fibre and electrical cables may be bundled together, and may be provided with optimised electromagnetic shielding. The received photo-acoustic electrical signals from the transducer array are amplified by the low noise amplifier 208, conditioned by the variable gain amplifier 210, followed by filtering by filter 212 to remove low frequency baseline oscillations due to human movements and other vibrations. The filtered signal is sampled by the analogue to digital converter 214 for further digital processing. A central control unit/first sensor processing module can be arranged to coordinate the laser trigger, data measurement, display, and other needed functionalities, as well as the blood oxygen saturation extraction from the measured PA and light signals.

FIG. 3 illustrates signal action in a region 202 of the subject. Light 110 is emitted to illuminate the region 202 of the subject and a target blood vessel 300. Induced photo acoustic signals 106 are picked up by photo-acoustic sensor 104. Scattered light signals 128 are picked up by the light sensor 126. Also illustrated are the skin layers of the epidermis 301, the dermis 302 and the blood vessel layer 304, erythrocytes 306 and blood for 308 as indicated.

As mentioned above, in at least one arrangement, the blood oxygen saturation value may be derived where the light source emits only light of a single wavelength. In this approach, both of the optical absorption induced photo-acoustic and diffusively scattered optical signals are collected to establish the equations discussed below. Based on the photo-acoustic signal equation and scattered optical equation, the inventors have found that it is possible to measure the blood oxygen saturation and the concentration of the oxygenated haemoglobin and deoxygenated haemoglobin using light of a single wavelength and within the safety range of the light source, such as a laser.

During a laser-induced photo-acoustic process, the acoustic signal is launched based on the principle of thermal expansion following the optical energy absorption by the sample. Here the blood vessel is the targeted object, we can acquire the photo-acoustic signal [31, 32].

$$P = G(\varepsilon_{HbO_2} C_{HbO_2} + \varepsilon_{HbR} C_{HbR}), \quad (1)$$

where G is related to the ultrasonic parameter, the system parameter, Gruneisen parameter and the local optical fluence which can be expressed as the multiplication of the local laser intensity and laser pulse width. These parameters are all constant for a fixed system setup and experimental environment. $\varepsilon_{HbO_2}$ and $\varepsilon_{HbR}$ are known molar extinction coefficients of oxygenated haemoglobin and deoxygenated haemoglobin, which are well documented. $C_{HbO_2}$ and $C_{HbR}$ are the unknown concentrations of oxygenated haemoglobin and deoxygenated haemoglobin. Therefore, the photo-acoustic signal has linear relation with the concentrations of two main kinds of haemoglobin in the blood.

That is, the photo-acoustic sensing apparatus 100 is configured to derive the de-correlated value 120 of blood oxygen saturation of the subject using a calibration coefficient, molar extinction coefficients of haemoglobin and scattering coefficients. Like molar extinction coefficients, these scattering coefficients are used to characterise specific materials like oxygenated hemoglobin or deoxygenated hemoglobin, which are assumed to be almost uniform among different people, though different people may show varying compositions of oxygenated hemoglobin and deoxygenated hemoglobin in blood. In short, the compositions may be different but the fundamental materials should be almost uniform.

On the other hand, when a beam of light irradiates on the surface of the sample, the light will be scattered and that is related to concentrations of oxygenated haemoglobin and deoxygenated haemoglobin by scattering coefficients $\mu_{HbO_2}$ and $\mu_{HbR}$ at certain wavelength, shown as $$I_s = H(\mu_{HbO_2} C_{HbO_2} + \mu_{HbR} C_{HbR}), \quad (2)$$

where H is related to system parameter and the local optical fluence. From the simultaneous linear equations (1) and (2), the blood oxygen saturation value, which is defined as $$SO2 = \frac{C_{HbO_2}}{C_{HbO_2} + C_{HbR}},$$

can be calculated as $$SO2 = \frac{I_s \varepsilon_{HbR} \eta - p\mu_{HbR}}{I_s \eta(\varepsilon_{HbR} - \varepsilon_{HbO_2}) + p(\mu_{HbO_2} - \mu_{HbR})}, \quad (3)$$

where $$\eta = \frac{G}{H}.$$

The two parameters need to be calibrated since they are both related to specific system setup and experimental environment. Thus, the photo-acoustic and scattered light signals at two different wavelengths are used for calibration. For wavelength $\lambda_1$, $$P(\lambda_1) = G(\varepsilon_{HbO_2}(\lambda_1) C_{HbO_2} + \varepsilon_{HbR}(\lambda_1) C_{HbR}), \quad (4)$$

$$I_s(\lambda_1) = H(\mu_{HbO_2}(\lambda_1) C_{HbO_2} + \mu_{HbR}(\lambda_1) C_{HbR}), \quad (5)$$

For wavelength $\lambda_2$, $$P(\lambda_2) = G(\varepsilon_{HbO_2}(\lambda_2) C_{HbO_2} + \varepsilon_{HbR}(\lambda_2) C_{HbR}), \quad (6)$$

$$I_s(\lambda_2) = H(\mu_{HbO_2}(\lambda_2) C_{HbO_2} + \mu_{HbR}(\lambda_2) C_{HbR}), \quad (7)$$

Calibrated SO2 can be calculated by dividing equation (4) with equation (6) as $$\langle SO2 \rangle_{Cal} = \frac{P(\lambda_2) \varepsilon_{HbR}(\lambda_1) - P(\lambda_1) \varepsilon_{HbR}(\lambda_2)}{P(\lambda_2)(\varepsilon_{HbR}(\lambda_1) - \varepsilon_{HbO_2}(\lambda_1)) - P(\lambda_1)(\varepsilon_{HbR}(\lambda_2) - \varepsilon_{HbO_2}(\lambda_2))}. \quad (8)$$

In this example, one of the calibration wavelengths is used as the single measurement wavelength, but that is not an essential requirement. The single measurement wavelength can be one which is not used in the calibration. But to save the wavelength and associated cost, it may be preferable the single measurement wavelength is used as one of the calibration wavelengths. For example, taking wavelength $\lambda_2$ as reference wavelength, the corresponding equations (5) and (7) have the same relation with equation (3). So from (3) and (8), we can obtain:

$$\eta = \frac{G}{H} = \frac{\langle SO2 \rangle_{Cal} \cdot P(\lambda_2)(\mu_{HbO_2}(\lambda_2) - \mu_{HbR}(\lambda_2)) + P(\lambda_2)\mu_{HbR}(\lambda_2)}{I_s(\lambda_2) \varepsilon_{HbR}(\lambda_2) - \langle SO2 \rangle_{Cal} \cdot I_s(\lambda_2)(\varepsilon_{HbR}(\lambda_2) - \varepsilon_{HbO_2}(\lambda_2))}. \quad (9)$$

Ultimately, wavelength $\lambda_1$ can be utilised as the single-wavelength laser illumination for SO2 detection and continuous monitoring with calibrated value $\eta$ $$\langle SO2 \rangle_{Mea} = \frac{I_s(\lambda_1) \varepsilon_{HbR}(\lambda_1) \eta - P(\lambda_1)\mu_{HbR}(\lambda_1)}{I_s(\lambda_1)\eta(\varepsilon_{HbR}(\lambda_1) - \varepsilon_{HbO_2}(\lambda_1)) + P(\lambda_1)(\mu_{HbO_2}(\lambda_1) - \mu_{HbR}(\lambda_1))}. \quad (10)$$

Thus, it will be appreciated that the photo-acoustic sensing apparatus 100 is configured to derive the de-correlated value 120 of blood oxygen saturation of the subject 102 using the sensed photo-acoustic signals 114 and the sensed scattered light signals 130 induced when the region of the subject 102 is illuminated by the light source 108, the light source emitting light 110 of a single wavelength. As mentioned above, in preferred arrangements the light source comprises a laser, such as a laser diode.

Starting from equation 3, and expanding the brackets of the denominator:

$$SO2 = \frac{I_s \varepsilon_{HbR} \eta - P\mu_{HbR}}{I_s \varepsilon_{HbR} \eta - P\mu_{HbR} + P\mu_{HbO_2} - I_s \eta \varepsilon_{HbO_2}}$$

Substitute equation 1, equation 2 and $$\eta = \frac{G}{H}:$$

$$SO2 = \frac{H\left(\frac{\mu_{HbO_2}C_{HbO_2}+}{\mu_{HbR}C_{HbR}}\right)\varepsilon_{HbR}\left(\frac{G}{H}\right) - G\left(\frac{\varepsilon_{HbO_2}C_{HbO_2}+}{\varepsilon_{HbR}C_{HbR}}\right)\mu_{HbR}}{H\left(\frac{\mu_{HbO_2}C_{HbO_2}+}{\mu_{HbR}C_{HbR}}\right)\varepsilon_{HbR}\left(\frac{G}{H}\right) - G\left(\frac{\varepsilon_{HbO_2}C_{HbO_2}+}{\varepsilon_{HbR}C_{HbR}}\right)\mu_{HbR} + \left(G\left(\frac{\varepsilon_{HbO_2}C_{HbO_2}+}{\varepsilon_{HbR}C_{HbR}}\right)\mu_{HbO_2} - H\left(\frac{\mu_{HbO_2}C_{HbO_2}+}{\mu_{HbR}C_{HbR}}\right)\left(\frac{G}{H}\right)\varepsilon_{HbO_2}\right)}$$

Expanding all the brackets:

$$SO2 = \frac{\begin{array}{c}G\varepsilon_{HbR}\mu_{HbO_2}C_{HbO_2} + G\varepsilon_{HbR}\mu_{HbR}C_{HbR} - \\ G\varepsilon_{HbO_2}\mu_{HbR}C_{HbO_2} - G\varepsilon_{HbR}\mu_{HbR}C_{HbR}\end{array}}{\begin{array}{c}G\varepsilon_{HbR}\mu_{HbO_2}C_{HbO_2} + G\varepsilon_{HbR}\mu_{HbR}C_{HbR} - \\ G\varepsilon_{HbO_2}\mu_{HbR}C_{HbO_2} - G\varepsilon_{HbR}\mu_{HbR}C_{HbR} + \\ (G(\varepsilon_{HbO_2}C_{HbO_2} + \varepsilon_{HbR}C_{HbR})\mu_{HbO_2} - \\ H(\mu_{HbO_2}C_{HbO_2} + \mu_{HbR}C_{HbR})\left(\frac{G}{H}\right)\varepsilon_{HbO_2})\end{array}}$$

$$SO2 = \frac{\begin{array}{c}G\varepsilon_{HbR}\mu_{HbO_2}C_{HbO_2} + G\varepsilon_{HbR}\mu_{HbR}C_{HbR} - \\ G\varepsilon_{HbO_2}\mu_{HbR}C_{HbO_2} - G\varepsilon_{HbR}\mu_{HbR}C_{HbR}\end{array}}{\begin{array}{c}G\varepsilon_{HbR}\mu_{HbO_2}C_{HbO_2} - G\varepsilon_{HbO_2}\mu_{HbR}C_{HbO_2} + \\ (G\varepsilon_{HbO_2}\mu_{HbO_2}C_{HbO_2} + G\varepsilon_{HbR}\mu_{HbO_2}C_{HbR} - \\ G\varepsilon_{HbO_2}\mu_{HbO_2}C_{HbO_2} - G\varepsilon_{HbO_2}\mu_{HbR}C_{HbR})\end{array}}$$

Simplifying the equation:

$$SO2 = \frac{G\varepsilon_{HbR}\mu_{HbO_2}C_{HbO_2} - G\varepsilon_{HbO_2}\mu_{HbR}C_{HbO_2}}{G\varepsilon_{HbR}\mu_{HbO_2}C_{HbO_2} - G\varepsilon_{HbO_2}\mu_{HbR}C_{HbO_2} + (G\varepsilon_{HbR}\mu_{HbO_2}C_{HbR} - G\varepsilon_{HbO_2}\mu_{HbR}C_{HbR})}$$

Factorising the equation by taking out common factors:

$$SO2 = \frac{GC_{HbO_2}(\varepsilon_{HbR}\mu_{HbO_2} - \varepsilon_{HbO_2}\mu_{HbR})}{GC_{HbO_2}(\varepsilon_{HbR}\mu_{HbO_2} - \varepsilon_{HbO_2}\mu_{HbR}) + GC_{HbR}(\varepsilon_{HbR}\mu_{HbO_2} - \varepsilon_{HbO_2}\mu_{HbR})}$$

Cancelling common factors G and $(\varepsilon_{HbR}\mu_{HbO_2} - \varepsilon_{HbO_2}\mu_{HbR})$:

$$SO2 = \frac{C_{HbO_2}}{C_{HbO_2} + C_{HbR}}$$

It is noted that SO2 is a ratio between oxygenated haemoglobin and total haemoglobin (deoxygenated+oxygenated).

As temperature related terms appear on both the numerator and denominator for calculating SO2, they cancel each other and make SO2 measurement inherently independent on the blood temperature. For the effects of blood glucose measurement on blood oxygen saturation, it should be noted that glucose concentration is far less (<1/1000) than that of haemoglobin in blood vessels and as a result, any fluctuations in glucose concentration will affect negligibly the photo-acoustic signals of the blood: in fact, a 1/1000 fluctuation caused by glucose concentration in blood is well below the system noise level since a blood oxygen saturation measurement accuracy of 1% is already known. Put it simply, glucose concentration is expected only to induce a measurement error well below 1% on blood oxygen saturation, which is likely not to be a concern at all.

Thus, the first sensor processing module 112 may be used to provide a de-correlated value 120 of blood oxygen saturation, where the term "de-correlated value" may be considered to mean that the effects of variations in one or both of blood core temperature and blood glucose have little or no bearing on the blood oxygen saturation monitoring value.

Figure 4A:
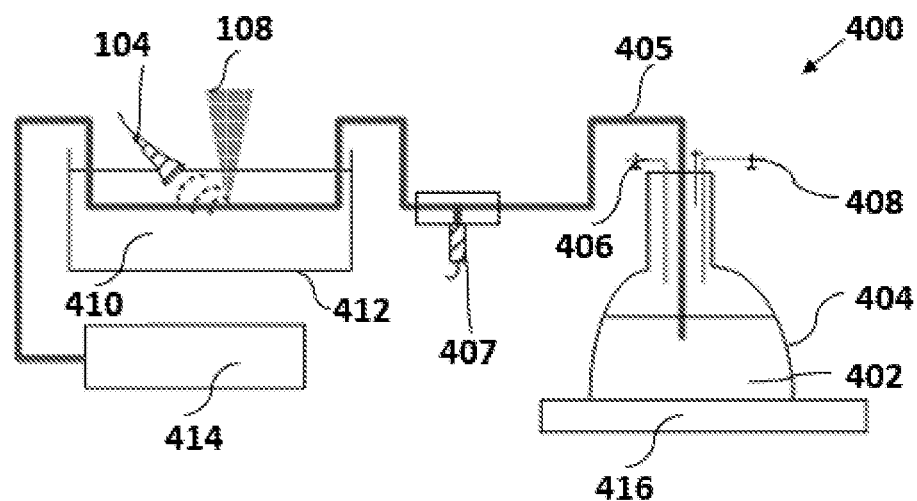
FIG. 4a is a schematic diagram illustrating the system architecture of an experimental setup implementing the technique of FIG. 2.
Figure 4B:
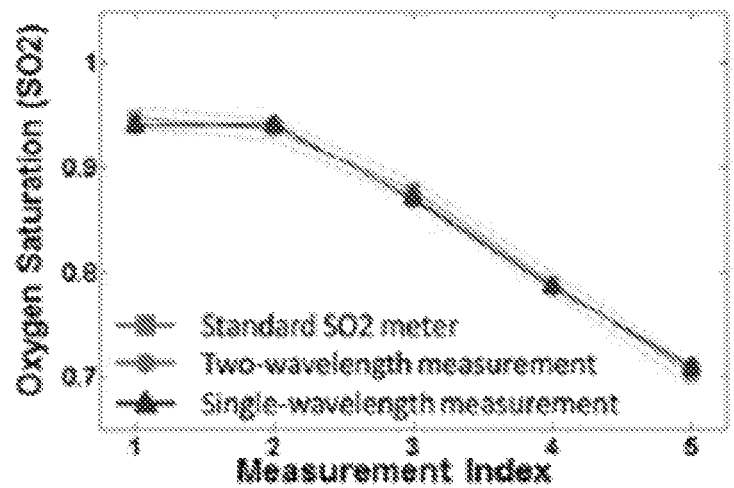

The feasibility of the technique was explored in an experimental setup 400 as illustrated in FIG. 4a. This utilises porcine blood for the validation. Fresh porcine blood 402 was collected and stored in a flask 404. A transparent tube 405 was used to export the blood to the water 410 in water tank 412 for photo-acoustic and scattered light measurement. The conical flask 404 was connected with an oxygen supply 406 and a carbon dioxide supply 408 to increase and decrease the SO2 in the blood respectively. To validate the measurement accuracy, a standard blood oxygen saturation meter 407 was utilised to monitor blood oxygen saturation inside the tube. One suitable blood oxygen saturation meter is the DO-166MT-1 meter from LAZAR Research Laboratories. FIG. 4b shows the blood oxygen saturation measurement by the standard SO2 meter, conventional two-wavelength measurement and the disclosed novel single-wavelength method. It illustrates that the disclosed single-wavelength measurement is capable of reaching within 1% accuracy.

Therefore, a photo-acoustic SO2 measurement method which may use a single-wavelength is disclosed. It differentiates from any existing methods which require at least two wavelengths. The technique may utilise and quantify both the scattering and absorption of light illumination which reflects the SO2 concentration, and the method can extract the SO2 parameters using, say, only one wavelength. Hence, the complexity and cost of the sensor can be significantly reduced, and make the computation close to real time. In addition, the method can also adopt multi-wavelength but will enhance the performance (in terms of accuracy, robustness) greatly when compared with existing multi-wavelength methods. With multiple wavelengths, it is possible to obtain a set of linear equations (called Set one equation) similar to Eq. (1), where the molar extinction coefficients $\varepsilon_{HbO_2}$ and $\varepsilon_{HbR}$ are different for each wavelength, but known according to existing tabulations. Then by applying a least square fitting algorithm, it is possible to obtain a more reliable estimate of SO2 solely from the Set one equation. The same could be done with Eq. (2) to yield a Set two equation and to solve a second SO2 value. One last potential improvement is do a simple averaging between the two SO2 values. Or more straightforwardly, a single least square fitting for Set one and Set two equations combined would suffice.

Therefore, additionally or alternatively, the photo-acoustic sensing apparatus 100 is configured to derive the de-correlated value of the blood oxygen saturation of the subject using the sensed photo-acoustic signals and the sensed scattered light signals induced when the region of the subject is illuminated by the light source, the light source emitting light of a plurality of wavelengths.

It is also to be noted that the above-described blood oxygen saturation monitoring technique may be provided separately, for example, in a dedicated sensor apparatus for deriving a de-correlated value of blood oxygen saturation of the subject.

Blood Core Temperature

FIG. 5 illustrates an exemplary architecture for a sensor processing module for deriving blood core temperature. In this example, a photo-acoustic sensor 104 comprises a patch sensor implementing a CMUT ultrasound transducer array to receive the PA signal. In the example, one or more compact laser diodes 108a and driver circuits 108b are used as the light source 108. While FIG. 5 illustrates three laser diodes 108a, other numbers, including one are contemplated. The output of the laser diodes are coupled efficiently into a fibre such as a 200 μm thick multimode fibre (MMF), through which the laser pulses are directed into the patch sensor. The patch sensor may also contain the distal end of fibre for delivering the laser light, and/or the head of electrical wire bundle for conveying the electrical signal of the transducer array. The laser light coming out from the fibre can either penetrate through the transducer array [33] or pass through a very small hollow that is made in the transducer. The electrical wires and the fibre may be wound together inside a thin wire that connects the main body of the device to the patch sensor.

Also in this example, the laser light is a directed towards the blood vessel 204 of the subject, having blood 206 flowing therethrough. Sensed photo acoustic signals 114 and sensed scattered light signals 130 are conveyed back to a low noise amplifier 208, and processed by a variable gain amplifier 210, a filter 212, an analogue to digital converter 214 and a DSP module 216 and a digital signal processing module 500 prior to being transmitted to second sensor processing module 116. It will be appreciated that, in this example, the processing electronics for the blood core temperature measurement derivation may use the components used for the same or similar purpose in the blood oxygen saturation measurement, as indicated by the reference numerals in FIG. 5, or separate stand-alone components may be used for each sensing technique.

The derived de-correlated value 122 of blood core temperature may be made available, for example, for display on a display, not shown (which may implement a GUI) or for onward transmission through transmitter 502. Advantageously, alarms module 506 may be provided.

As mentioned above, in this example in the light source comprises a laser, such as a photodiode 108a which emits a laser beam 220 to fibre coupler 222 which couples the laser light signal into fibre 224.

Such an arrangement may require only a small size (less than 1 cm2) and lightweight patch sensor to be attached tightly onto a human body (e.g. at the neck and/or close to the chest) to receive the photo-acoustic signal whereas the main-body of the device can be comfortably carried in other parts of the human body. After firing of the laser diodes, the generated photo-acoustic signal that carries rich information about the interrogated tissue, including core temperature (at, for example, the main blood vessels of the carotid and pulmonary arteries), is first amplified by the low noise amplifier and then further conditioned by the variable gain amplifier, followed by filtering to remove low frequency baseline oscillations caused by human movements and other vibrations. The filtered signal is sampled by an analogue to digital converter for further processing in one or more, for example, low power digital signal processors DSP. Second sensor processing module 116 coordinates the measurement, display, alert and other needed functions.

The wavelength of 808 nm ($\lambda_0$) is chosen here, although other wavelengths are also suitable. For deeper penetration, the workable wavelength range may be in the NIR part of the spectrum, ranging from around 700 nm to around 1200 nm. Falling into the human body window, the near infrared wavelength is allowed for deep penetration and a higher irradiation dose up to 100 mJ/cm$^2$ can be used based on ANSI safety standards [34]. The availability of high power laser diodes at this range contributes another justification, which allows a customised laser sequence. Equally importantly, the 808 nm laser is the isosbestic point where oxygenated haemoglobin and deoxygenated haemoglobin show the same absorption, thus selection of this wavelength is advantageous for measuring temperature independently of the blood oxygenation.

Figure 6:
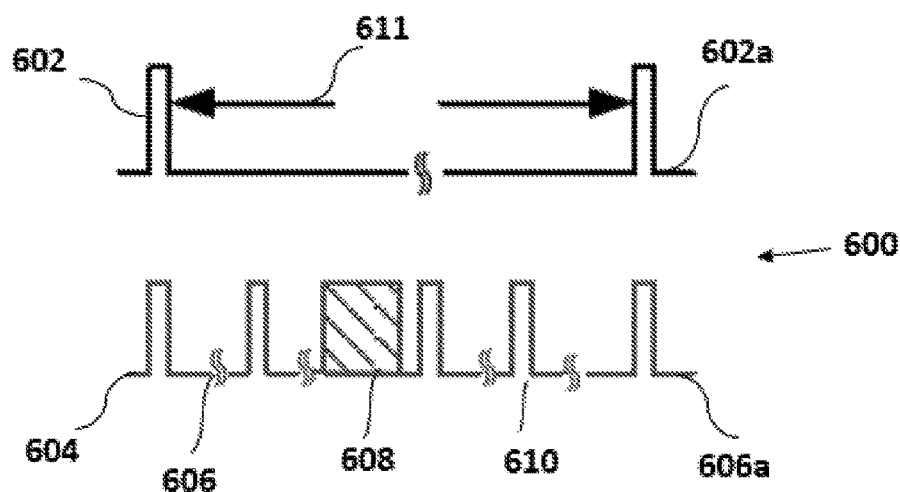
FIG. 6 is a sequence of timing diagrams illustrating exemplary pulse sequences for the arrangement of FIG. 5.

The timing sequence 600 for the operation of light source (laser diodes) is given in FIG. 6. With a trigger signal 602 to initiate measurement, the 808 nm laser diode works in a first photo-acoustic mode and is driven by the driver circuit to fire consecutively a train/sequence 604 of laser pulses at the repetition rate of, for example, 1 kHz. The interval 606 of operation in the first photo-acoustic mode of operation is illustrated. The photo-acoustic signals may be subsequently stored. Then, the laser diode 108 is driven into a second perturbation mode of operation, having an interval 608. In this example, the perturbation mode is a heating mode for perturbing the temperature of the probed region, for example by a relatively small amount. It is also feasible to use an ultrasonic transmitter emitting, for example a high-intensity ultrasound signal to perturb the temperature and in order to provide sufficient accuracy without raising safety issues. The temperature rise may be in the order of around 1 to around 4 degree Celsius. This perturbation interval 608 is followed by returning to the first photo-acoustic mode for a second interval 610 for a second measurement with a train of laser pulses. A second trigger pulse 602a restarts the sequence of first photo-acoustic mode, perturbation mode then first photo-acoustic mode again, reverting to another instance of the first interval 606a of operation in the first photo-acoustic mode. The perturbation is explained later. In one arrangement, 40 times of laser pulses in the train is determined in order to achieve an accuracy of 0.075 degrees Celsius for the temperature measurement [8]. The amplitude of the photo-acoustic signal is:

$$P(\lambda_0)=[C_{HbO_2}(T_1)+C_{HbR}(T_1)]\varepsilon_{Hb}(\lambda_0)\Gamma(T_1)F=\varepsilon_{Hb}(\lambda_0)\Gamma(T_1)FC_{Hb}(T_1), \quad (11)$$

where $\varepsilon_{Hb}(\lambda_0)$ is the known molar extinction coefficient of oxygenated haemoglobin and deoxygenated haemoglobin. $C_{HbO_2}(T_1)$ and $C_{HbR}(T_1)$ are oxygenated and deoxygenated haemoglobin concentration in blood at temperature $T_1$. $C_{Hb}(T_1)$ is the total haemoglobin concentration. $\Gamma(T_1)$ is the Grueneisen parameter at $T_1$ and F is the laser fluence at the blood vessel. The temperature measurement is based on the fact that $\Gamma(T)$ is linear to absolute temperature stated as: $\Gamma(T)=A+BT$ where A and B are constants determined by material properties. With a known reference point $P(T_0)$ from device calibration, absolute temperature can be calculated from PA measurement P as $$T = \frac{P}{P(T_0)}\left(\frac{A}{B}+T_0\right)-\frac{A}{B}, \quad (11a)$$

assuming the concentration is constant. The measurement accuracy on the amplitude of the photo-acoustic signal is directly translated to the accuracy of temperature probing. However, it is observed in Eq. (11) that the amplitude is affected by the total haemoglobin concentration $C_{Hb}$ ($T_1$) that interferes with temperature measurement. To rectify the $C_{Hb}$ ($T_1$) fluctuation induced by inevitable human metabolism, the active perturbation method is proposed by designing an innovative laser diode excitation sequence. Suppose both of the temperature and haemoglobin concentration are changed during physical activities and the PA signal is affected by both of them. At isosbestic wavelength of $\lambda_0$, $P(T_2)=\varepsilon_{Hb}(\lambda_0)C_{Hb}(T_2)\Gamma(T_2)F$, where the total haemoglobin concentration $C_{Hb}$ ($T_2$) at temperature $T_2$ is different from $C_{Hb}$ ($T_1$). When the laser diode is turned into perturbation (heating) mode (for example, low power continuous mode) with a fluence rate $F_2$ at blood vessel for a short time $\Delta t$, the temperature of blood is slightly perturbed by $\Delta T$. An immediate second session of photo-acoustic signal acquisition is then made: $P(T_2+\Delta T)=\varepsilon_{Hb}(\lambda_0)C_{Hb}(T_2+\Delta T)\Gamma(T_2+\Delta T)F$. When $\Delta t$ is quite small (less than 1 second), the total haemoglobin concentration variation during this time interval can be ignored, i.e. $C_{Hb}(T_2+\Delta T)=C_{Hb}(T_2)$. Taking the pressure difference $$\Delta P(T_2)=P(T_2+\Delta T)-P(T_2)=\varepsilon_{Hb}(\lambda_0)FBC_{Hb}(T_2)\Delta T \quad (11b)$$

to normalize the measurement of $P(T_2)$, we get $$P_N(T_2) = \frac{P(T_2)}{\sqrt{\Delta P(T_2)}} = \sqrt{\frac{FC_p}{F_2 B}}\,\Gamma(T_2) = A' + B' T_2. \quad (11c)$$

$C_p$ is the heat capacity of haemoglobin; $A'=A\sqrt{FC_p/(F_2 B)}$ (11d) and $B'=\sqrt{BFC_p/(F_2)}$ (11e) are new constants.

Temperature increment $\Delta T$ is calculated as absorbed light energy ($\varepsilon_{Hb}(\lambda_0)C_{Hb}(T_2)F_2$) divided by the heat capacity $C_P$, namely $$\Delta T=\varepsilon_{Hb}(\lambda_0)C_{Hb}(T_2)F_2/C_p \quad (11f)$$

Therefore, the temperature can be measured without interferences of other varying physiological parameters by using the normalized PA signal $P_N(T_2)$. It is noted here that the temperature increment $\Delta T$ should be small enough to avoid undesirable safety issues while large enough to produce a noticeable effect on the immediate PA signal generation.

Calibration may not be necessary during absolute temperature calculation with $P_N(T_2)$, and to be on the safe side, one-time calibration is likely to be enough upon first time usage, meaning further calibration afterwards is not necessary. Recalling that $A'=A\sqrt{FC_p/(F_2 B)}$ and $B'=\sqrt{BFC_p/(F_2)}$, an obstacle to achieve absolute temperature is the ratio $F/F_2$ since $C_p$ is known constant while A and B, as material constants, can be known by either ex vivo calibration or using established values. In fact F and $F_2$ are likely to be unknown at depths inside tissue. However, the light transfer function from the same laser diode used to deliver F and $F_2$ toward any location inside the tissue is the same for both photo-acoustic mode and heating/perturbation mode laser firing, despite intricate scattering processes. Hence, $F/F_2$ can be written as $$\frac{F}{F_2} = \frac{S(r) \times W_1 \times \Delta t_p}{S(r) \times W_2 \times \Delta t} = \frac{W \Delta t_{p1}}{W_2 \Delta t} = \frac{I_1 \Delta t_{p1}}{I_2 \Delta t}, \quad (11g)$$

where S(r) is the light transfer function from the laser diode to location r, $\Delta t_{p1}$ is the known laser pulse duration in PA mode; $W_1$ and $W_2$ are the power of laser diode working photo-acoustic mode and heating/perturbation mode. $I_1$ and $I_2$ are the current supplied to the laser diode in each mode those are readily obtainable values in the driving circuits and ultimately, making $F/F_2$ known. Thus, A' and B' can be obtained either with calibration (measuring directly A' and B' via ex-vivo experiments for the specific material or using similar materials from animals, as done in some literature) or preferably, using established material constant value of A and B). Finally, absolute temperature is inferred from the measurement of $$P_N(T) \text{ as: } T = \frac{P_N(T) - A'}{B'}. \quad (11h)$$

In short, this novel perturbation method utilising an innovative laser firing sequence may enable absolute core temperature measurement without requiring calibration.

It may also be more resistant to interferences of other physiological parameters like haemoglobin concentration.

Thus it will be appreciated that the second sensor processing module 116 is configured: to derive a first photo-acoustic value (e.g. $P(\lambda_0)$ from Equation 11) when the region 202 of the subject 102 is subjected to illumination by the light source 108 operating in a first signal acquisition mode of operation (e.g., the first photo-acoustic mode of operation in interval 606), and emitting light 110 of an isosbestic wavelength; to derive a second photo-acoustic value (e.g. $P(T_2+\Delta T)$ from Equation 11) when the region of the subject is subjected to illumination by the light source operating in the first signal acquisition mode of operation, after having been subjected to illumination by the light source operating in a second perturbation mode of operation (e.g. the second heating interval 608); to derive a pressure difference value (for example $\Delta PT_2$ from Equation 11b) from the first photo-acoustic value and the second photo-acoustic value; to derive a normalised second photo-acoustic value (for example $P_N(T_2)$ from Equation 11 c) using the second photo-acoustic value and the pressure difference value; and to derive the de-correlated value of blood oxygen saturation of the subject using the normalised second photo-acoustic value, a first blood core temperature constant (for example, A') and a second blood core temperature constant (B'), and this may be done, for example, using equation 11h.

It will also be appreciated that, in this example, the light source 108 comprises a laser, and the second sensor processing module 116 is configured to derive the first blood core temperature constant A' using: a first material property constant (A); a second material property constant (B); a first current value $I_1$ for current supplied to the laser during the first signal acquisition mode of operation; a second current value $I_2$ for current supplied to the laser during the second perturbation mode of operation; a laser pulse duration $\Delta t_{pI}$ in the first signal acquisition mode of operation; a duration of the second perturbation mode of operation $\Delta_t$; and a heat capacity of haemoglobin $C_p$. In this example, second sensor processing module 116 uses equations 11d and 11g in this calculation.

In this example, the second sensor processing module 116 may also be configured to derive the second blood core temperature constant B' using: the second material property constant B; the first current value $I_1$ for current supplied to the laser during the first signal acquisition mode of operation; the second current value $I_2$ for current supplied to the laser during the second perturbation mode of operation; the laser pulse duration $\Delta t_{pI}$ in the first signal acquisition mode of operation; the duration of the second perturbation mode of operation $\Delta_t$; and the heat capacity of haemoglobin $C_p$. In this example, the second sensor processing module 116 uses equations 11e and 11g in this calculation.

It will also be appreciated that, additionally or alternatively (and as mentioned above), the photo-acoustic sensing apparatus is configured to obtain one of the first blood core temperature constant A' and the second blood core temperature constant B' during a calibration process.

Similar to SO2 measurement, the temperature measurement in the blood is at least largely and possibly completely immune to glucose concentration variations due to its exceedingly low concentration. For interference from SO2, there is a much simpler solution, as described above. Note that the proposed temperature measurement uses only one wavelength and that for blood, there are several special wavelengths where deoxygenated haemoglobin and oxygenated haemoglobin have the same light absorbing coefficient. These wavelengths are called isosbestic wavelengths. Therefore, by using isosbestic wavelengths, no matter how SO2 changes, the blood photoacoustic signals (thus the temperature measurement) will not be affected. While the total concentration of haemoglobin may change, the proposed method that adopts a unique laser sequence for absolute temperature measurement employs a normalization method as well, which makes it independent on the haemoglobin concentration.

Thus, the second sensor processing module 116 may be used to provide a de-correlated value 122 of blood core temperature, where a "de-correlated value" may be considered to mean that the effect of variations in one or both of blood oxygen saturation and blood glucose have little or no bearing on the blood core temperature monitoring value.

Figure 7A:
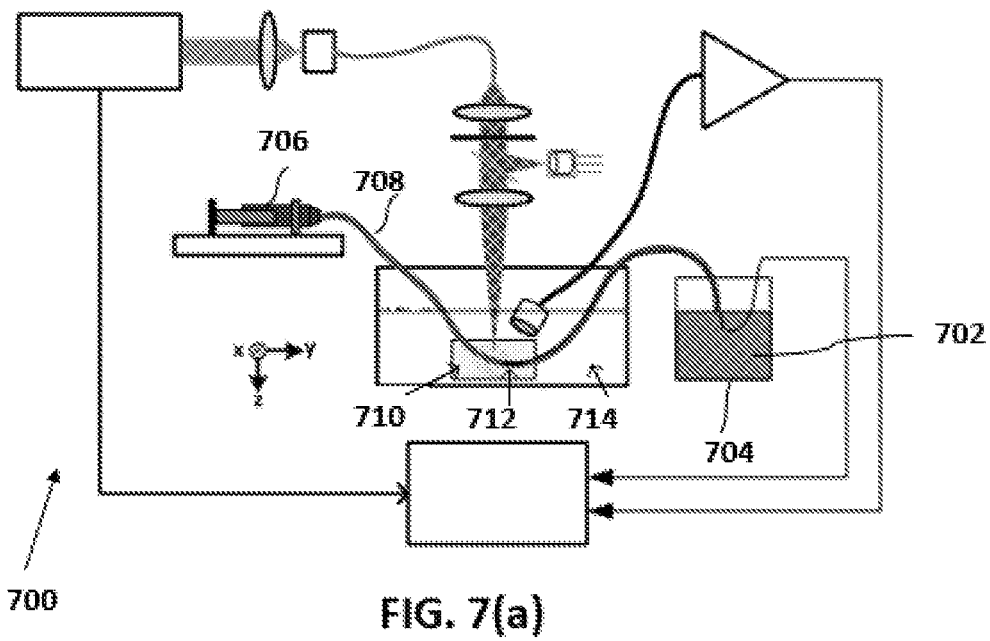
FIG. 7a is a schematic diagram illustrating the system architecture of an experimental setup implementing the technique of FIG. 5.
Figure 7B:
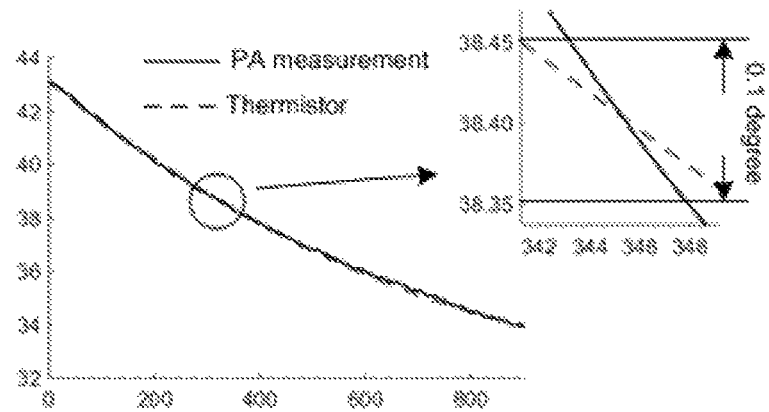

The feasibility of the technique was explored in an experimental setup 700 as illustrated in FIG. 7a. This utilises porcine blood for the validation. Fresh porcine blood 702 was collected and stored in a flask/container 704. A syringe pump 706 was used to pump the porcine blood into a tube 708 with a diameter of 5 mm and embedded in a block 710 of fat tissue with thickness of 2 cm. The absolute temperature is monitored by a thermistor 712 that is directly inserted into the blood tube for measurement comparison. The temperature is changeable by placing the tissue phantom in hot water 714 and allowing it to cool down naturally. Experimental results by the photo-acoustic method and thermistor are shown in FIG. 7(b), which indicates that an accuracy of <0.1 degree Celsius may be achieved.

Thus, a photo-acoustic based blood core temperature measurement method is proposed where an active perturbation method is used by designing an innovative laser diode excitation sequence to probe temperature independently of haemoglobin concentration. Moreover, the absolute temperature can be determined by either without calibration or with only one-time calibration upon first usage.

It is also to be noted that the above-described blood core temperature monitoring technique may be provided separately, for example, in a dedicated sensor apparatus for deriving a de-correlated value of blood core temperature of the subject.

Blood Glucose

FIG. 8 illustrates an exemplary architecture for a sensor processing module for deriving blood glucose. In this example, the photo-acoustic sensor 104 comprises a microphone for receiving the photo-acoustic signal. In the example, a plurality of compact laser diodes 108a and the driver circuit 108b are used as a light source 108. While FIG. 8 illustrates three laser diodes 108a, other numbers, including two (where two wavelengths are required, as described below), are contemplated. The output of the laser diodes, each of which may emit at distinct wavelengths, are coupled into a fibre through which the laser pulses are directed at the region 202 of the subject 102, in this example, a finger of the subject, with the laser pulses directed into the skin by efficiently coupling the output of the laser diodes 108a with a series of lens and mirrors into the photo-acoustic cell 104. During measurement, the fingertip may be in contact with the photo-acoustic cell and the generated photo-acoustic signal after the firing of the laser diodes travels back and forth in the cell, which amplifies the signal substantially. The boosted signal is sensed by the acoustic microphone, further amplified by a low noise amplifier 208, conditioned by a variable gain amplifier 210 and bandpass filter 212, sampled by an analogue to digital converter 214 and subsequently processed in a low power DSP module 500. The bandpass filter may be included for reducing noise and removing low frequency baseline oscillations. The function of the third sensor module 118 includes coordinating the timing sequence of laser diodes, spectrum calculations by DSP, and providing display.

The proposed solution illustrated may be a portable PA-based device featuring a glucose measurement cell that fits and contacts with the fingertip or other sites under the subject's skin. Interstitial fluid of the skin may be examined by the device. The rationale for selecting skin as the measurement medium is that its interstitial fluid, which reflects blood glucose level, is the body fluid closest to the surface of the body. Though other body fluids are accessible, such as saliva, tears, and urine, they show either no correlation with blood glucose or exhibit a long delay with respect to variations in blood glucose levels (hours in the case of tears). Glucose holds only a minuscule share in the haemoglobin-dominant blood, making it difficult to be directly measured in practice or by non-invasive methods like NIRS. Moreover, the fact that blood contains a more complicated matrix compared to interstitial fluid amounts to increased interference from other components of blood. Given these constraints, the interstitial fluid of skin that contains fewer components while reflecting blood glucose well is therefore an appealing option. The skin structure is given in FIG. 3 and the various layers of the epidermis are the stratum corneum, the stratum granulosum and the stratum spinosum. The interstitial fluid comprises albumin, glucose and some traces of lactate are found in the stratum spinosum, which is located at a superficial depth of about 15-20 μm. The glucose level in the interstitial fluid correlates with the level in blood, with a latency of change of only several minutes. Hence, by detecting the glucose level in, for example, the epidermis, in vivo blood glucose levels can be effectively measured.

Figure 9:
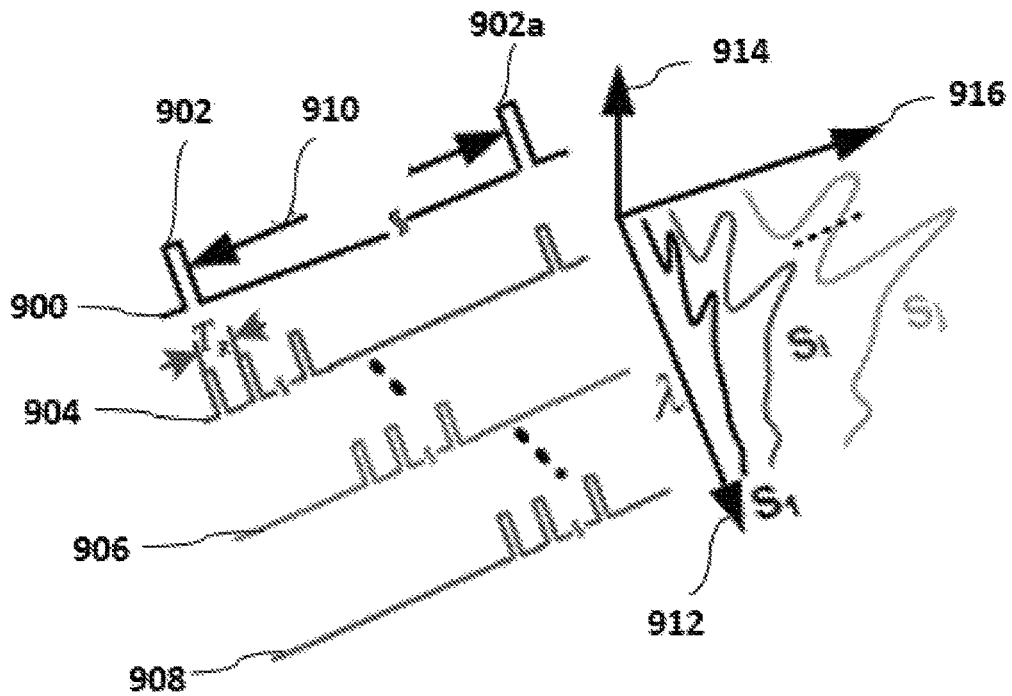
FIG. 9 is a sequence of timing diagrams illustrating exemplary pulse sequences for the arrangement of FIG. 8.

Plural, perhaps several wavelengths in the visible and/or near infrared range may be chosen for the photo-acoustic spectroscopy measurement of glucose and the monitoring sequence is given in FIG. 9. Firstly, the superficial vein is identified, for example either by vision or by a photo-acoustic imaging method. After that, the spectroscopy sweeps the wavelengths and records the photo-acoustic response at each disparate wavelength. In one photo-acoustic guided transmission spectroscopy (PGTS) method, each wavelength is fired N times and the duration between each firing is $T_R$. $T_R$ determined by the resonance frequency of the photo-acoustic cell so that the photo-acoustic signal sequence would have a coinciding. N, on the other hand, has more freedom to choose compared to $T_R$. However, in order to gain a high signal to noise ratio measurement, N should be close to the qualify factor Q of the cell for the resonance to build up effectively. Though bulky tunable near infrared lasers are commercially available, laser diodes offer the advantages of a more compact size and wider wavelength range. The glucose concentration can be calculated from the measured photo-acoustic signals at all adopted wavelengths.

Figure 10:
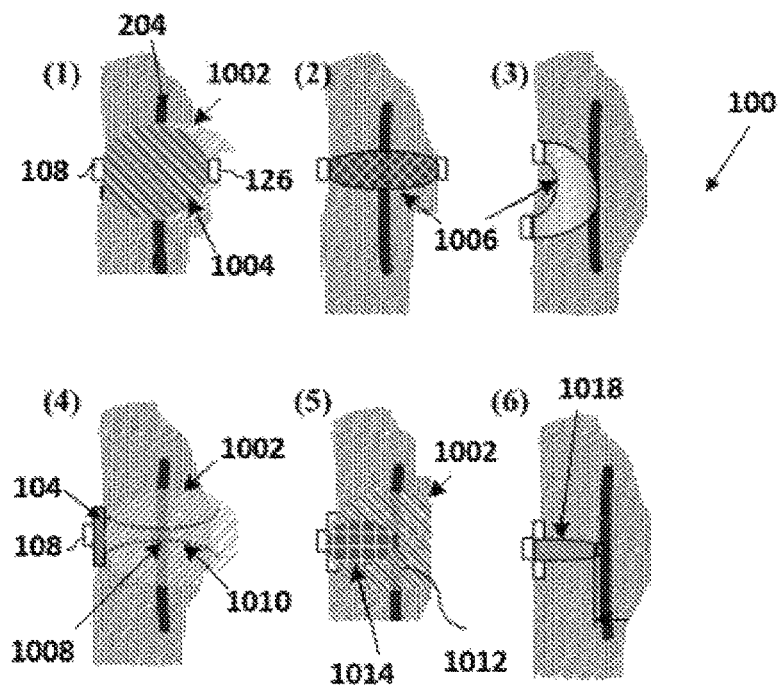
FIG. 10 is a series of views illustrating exemplary arrangements for the arrangement of FIG. 8.

A briefing on the conventional transmission or reflection of near infrared spectroscopy technique is given first for better appreciation of the PA guided transmission method. As shown in FIG. 10(1), light emitted from the laser diode is scattered upon entering the tissue. Its spatial distribution can be modelled by diffuse equation and represented by the spatial sensitivity function of the laser diode, $S_{LD}(r)$. Similarly, the photodiode placed on the other side that collects the transmitted light has a spatial sensitivity function of $S_{PD}(r)$, meaning that the photons travelled in that region can be collected effectively. Therefore, from the emission of laser diode (source) to the reception of photodiode (detector), the tissue region covered by both $S_{LD}(r)$ and $S_{PD}(r)$ is probed by the photons, and perhaps only this region. This particular region and its associated spatial weighting are characterized by the source-detector spatial sensitivity function, which is calculated as $S(r)=S_{LD}(r) \times S_{PD}(r)$. FIG. 10(2) and FIG. 10(3) depict the spatial sensitivity function for the transmission and reflection configurations respectively. The limitations therein for the transmission method are its limited access points and the fact that, for glucose measurement, the more abundant haemoglobin of vasculature can mask glucose in the blood and skin layer. For reflection, though it is more accessible to tissue site, the interferences from haemoglobin persists.

For the proposed photo-acoustic guide transmission method, the superficial vein beneath the skin is exploited as the "guide star" for measuring the glucose level inside the skin layer. Shown in FIG. 10(4), the light propagation from laser diode to tissue is the same, i.e. $S_{LD}(r)$ remains. However, the ultrasound transducer replaces the photodiode to receive the photo-acoustic signals generated from the vein in the proposed method. Since the photo-acoustic signal is proportional to the number of photons reaching the vein, it essentially measures the light intensity therein, and this can be considered like putting a photodiode at the vein inside the tissue. It is then equivalent to a virtual photodiode. The size of the photodiode is determined by the intersection of the vein and the radiation pattern of the ultrasound transducer, which is indicated by a black circle in FIG. 10(4). Then shown as an analogy in FIG. 10(5), the virtual photodiode has a spatial sensitivity function of $S'_{PD}(r)$, making the source-detector spatial sensitivity function to be $S'(r)=S_{LD}(r) \times S'_{PD}(r)$, which is depicted in FIG. 10(6). Since the resolution of the ultrasound transducer is scalable, the virtual photodiode is also scalable in size and can be made much smaller than the size of a real photodiode. This feature, coupled with the fact that the virtual photodiode enables a shorter distance between source and detector, makes $S'(r)$ occupying a smaller tissue volume and thus improves the spatial resolution compared to conventional NIRS.

To analyse mathematically, the optical fluence at the skin surface is denoted as $F_0$ and the effective scattering coefficient and absorption coefficient as $\alpha_s$ and $\alpha_a$ respectively, the laser fluence at the vein is: $F=\exp(-\alpha_s l-\alpha_a l)F_0$, where l is the distance of from the skin surface to the vein. Then the generated photo-acoustic signal by the vein is calculated as $P_v=\exp(-\alpha_s l-\alpha_a l)F_0\mu\Gamma$, with $\mu$ representing the absorption coefficient of the blood of laser light and $\Gamma$ representing the Grueneisen parameter. The PA signal can be re-expressed as $P_v=\exp(-\alpha_s l)F_0\mu\Gamma\exp(-\alpha_a l)=P_{v0}\exp(-\alpha_a l)$, where $P_{v0}$ is the artificial photo-acoustic signal that is generated when the concentration of molecules that absorb light is zero. Further still, it can be re-written as [31]

$$P_v=P_{v0}\exp(-\varepsilon_g C_g l), \quad (12)$$

where $\varepsilon_g$ is the molar absorption coefficient of glucose and $C_g$ is glucose concentration in the path. Then by monitoring PA signal $P_v$ after a calibration that extracts $P_{v0}$, concentration variations of the absorbing molecules like glucose can be measured as $$C_g = \frac{-\ln P_v/P_{v0}}{l\varepsilon_g}, \quad (13)$$

Note that the ranging capability of PA is able to render a reliable l.

The above rationale depends on the stability of the "guide star" (the vein) generated PA signal $P_{v0}$, which is affected by the strong scattering of skin and the possible blood haemoglobin concentration variation inside the vein. As the scattering of the skin is more determined by the relatively stable skin microstructures therein and considering the fact that the glucose concentration consists only a minor part of the interstitial fluid, the scattering coefficient is assumed to be affected negligibly by the glucose concentration. The "guide star" stability, however, is of more concern since the haemoglobin concentration may vary. As such, the solution proposed here is to choose a wavelength at which skin (including glucose and other molecules) exhibits poor absorption when compared with the haemoglobin to monitor the fluctuation of haemoglobin concentration inside the vein. Then another wavelength that exhibits strong absorption by glucose is added to monitor the glucose concentration in the skin. The process is elaborated below.

The haemoglobin concentration is monitored by the isosbestic wavelength ($\lambda_0$) for the oxygenated haemoglobin and deoxygenated haemoglobin so that the total haemoglobin concentration is accounted. The photo-acoustic signal for this wavelength is $$P_{v\lambda 0}=P_{v0\lambda 0}\exp(-\alpha_{a\lambda 0}l)=F_0\Gamma(\varepsilon_{H\lambda 0}C_H)\exp(-\alpha_{a\lambda 0}l), \quad (13a)$$

where $\varepsilon_{H\lambda 0}$ and $C_H$ are the molar absorption and total concentration of haemoglobin respectively. Suppose a fluctuation of $\Delta C_H$ in $C_H$ is present, then $$P_{v\lambda 0}=F_0\Gamma\varepsilon_{H\lambda 0}C_H(1+\Delta C_H/C_H)\exp(-\alpha_{a\lambda 0}l)=P_{v0\lambda 0}(1+\Delta C_H/C_H)\exp(-\alpha_{a\lambda 0}l). \quad (13b)$$

The fluctuation of haemoglobin concentration is therefore encoded at this wavelength and can be used to correct later measurements. Subsequently, a second wavelength that shows much stronger glucose absorption is used to detect glucose concentration, with the associated uncorrected PA signal being $$P_v(\lambda_1)=P_{v0\lambda 1}(1+\Delta C_H/C_H)\exp(-\alpha_{a\lambda 1}l) \quad (13c)$$

A simple normalization of $P_v(\lambda_1)$ by $P_v(\lambda_0)$ will correct the "guide star" fluctuation as $$PN_v(\lambda_1) = \frac{P_{v0\lambda 1}}{P_{v0\lambda 0}}\exp[-(\alpha_{a\lambda 1}-\alpha_{a\lambda 0})l] \quad (13d)$$

Since glucose molar absorption at wavelength $\lambda_0$ ($\varepsilon_{g\lambda 0}$) is much smaller than that at wavelength $\lambda_1$ ($\varepsilon_{g\lambda 1}$), then at concentration of $C_g$, glucose absorption coefficient for wavelength $\lambda_0$ ($\alpha_{a\lambda 0}=\varepsilon_{g\lambda 0}C_g$) is thus much smaller than ($\alpha_{a\lambda 1}=\varepsilon_{g\lambda 1}C_g$), that is $\alpha_{a\lambda 0} \ll \alpha_{a\lambda 1}$. Therefore $PN_v(\lambda_1)$ can be further reduced to $$PN_v(\lambda_1) \approx \frac{P_{v0\lambda 1}}{P_{v0\lambda 0}}\exp(-\alpha_{a\lambda 1}l) = \frac{P_{v0\lambda 1}}{P_{v0\lambda 0}}\exp(-\varepsilon_{g\lambda 1}C_g l) \quad (13e)$$

Take the logarithm on both sides of the equation so that we have $$\ln PN_v(\lambda_1) = \ln\left(\frac{P_{v0\lambda 1}}{P_{v0\lambda 0}}\right) - \varepsilon_{g\lambda 1}C_g l \quad (14)$$

One additional bonus for such a normalisation procedure is that it is insensitive to temperature because slow temperature drift is eliminated by the normalization so long as the "guide star" measurement of haemoglobin concentration and the glucose monitoring are always conducted in conjunction, making it particularly advantageous compared to other technologies like NIRS. Assume a temperature variation of $\Delta T$, then the two PA signals can be collectively written as:

$P_v(\lambda_i, \Delta T)=P_{v0\lambda i}(1+B\Delta T)(1+\Delta C_H/C_H)\exp(-\alpha_{a\lambda i}l)$ with i=0,1 and B as a constant. Obviously, normalisation of the two measurements eliminates the temperature effect in $PN_v(\lambda_1)$, which enables a temperature independent probing of glucose.

Multi-wavelength PA measurement (spectroscopy) may also be used. The more abundant water, fat and proteins in the skin are common interferences for glucose measurement via optical methods. To render an accurate and reliable glucose monitoring, decoupling of these interferences may be desired. Spectroscopy is a powerful technique to solve such a problem as the absorption spectrum of these materials are distinct, as the spectrum given in FIG. 11. Choosing M wavelengths for the measurement, the concentration of glucose can be extracted as follows. Denoting the molar absorption of specific molecule at wavelength $\lambda_i$ as $\varepsilon_i(\lambda_i)$ so that at glucose concentration $C_i$, the absorption is: $\mu_i(\lambda_i) = C_i\varepsilon_i(\lambda_i)$, i=1, 2 . . . , M. Then photo-acoustic signals, after normalisation by the "guide star" photo-acoustic measurement at all adopted wavelengths, can be expressed in a matrix format as:

$$\ln[PN_v(\lambda_1) \; PN_v(\lambda_2) \; \ldots \; PN_v(\lambda_M)] = [k_1 \; k_2 \; \ldots \; k_M] \quad (15)$$

$$-l \times [C_1 \; C_2 \; \ldots \; C_M] \times \begin{bmatrix} \varepsilon_1(\lambda_1) & \varepsilon_1(\lambda_2) & \ldots & \varepsilon_1(\lambda_M) \\ \varepsilon_2(\lambda_1) & \varepsilon_2(\lambda_2) & \ldots & \varepsilon_2(\lambda_M) \\ \ldots & \ldots & \ldots & \ldots \\ \varepsilon_M(\lambda_1) & \varepsilon_M(\lambda_2) & \ldots & \varepsilon_M(\lambda_M) \end{bmatrix},$$

where $$k_i = \ln\frac{P_{v0\lambda i}}{P_{v0\lambda 0}}$$

are system constants for each wavelength and can be obtained by a one-time calibration procedure. Solving the matrix will then reveal the concentration of various materials, including glucose, water and the glucose reading, which is now robust being decoupled to a large extent from those common interferences. It is noted here that with plenty of multivariate analysis methods like principal component analysis available, both the concentration and absorption matrix can be reconstructed from the PA measurements [12]. Generally, the absorption matrix is a priori knowledge, which can facilitate the calculations substantially.

Thus it will be appreciated that the third sensor processing module 118 is configured to derive a first glucose photo-acoustic value (for example, $P_{v\lambda 0}$ using equation 13b) when the region of the subject is subjected to illumination by the light source emitting light at a first wavelength, the first wavelength being selected for exhibiting a higher absorption in haemoglobin than absorption in glucose; to derive a second glucose photo-acoustic value (for example, $P_v(\lambda_1)$ using equation 13c) when the region of the subject is subjected to illumination by the light source emitting light at a second wavelength, the second wavelength being selected for exhibiting a higher absorption in glucose; to derive a corrected second glucose photo-acoustic value (for example, $PN_v(\lambda_d)$ using equation 13d) by normalising the second glucose photo-acoustic value using the first glucose photo-acoustic value; and to derive the de-correlated value of blood glucose of the subject using the corrected second glucose photo-acoustic value (using, for example, equation 14, optionally by rearranging the equation accordingly).

It will also be appreciated that the light source 108 comprises a laser, and the third sensor processing module 118 module is configured to derive the first glucose photo-acoustic value for blood in a blood vessel of the subject, the first glucose photo-acoustic value being related to: a laser fluence value $F_0$ for the laser operation at the first wavelength; a molar absorption coefficient $\varepsilon_{H\lambda 0}$ for haemoglobin at the first wavelength; a total concentration of haemoglobin $C_H$ in the blood; an absorption coefficient $\alpha_{a\lambda 0}$ for skin of the patient; and a distance l between a surface of skin of the patient and the blood vessel.

Further, the third sensor processing module 116 may be configured to derive the second glucose photo-acoustic value for blood in the blood vessel of the subject, the second glucose photo-acoustic value being related to: the total concentration of haemoglobin $C_H$ in the blood; the absorption coefficient $\alpha_{a\lambda 0}$ for skin of the patient; and the distance l between the surface of skin of the patient and the blood vessel.

For the glucose measurement, blood oxygen saturation fluctuations will be significant since we use blood vessels as the "guide star" in our proposed PGTS method. Yet, as derived mathematically above, two wavelengths (thus a spectroscopic method) or more can be used to decouple both the blood oxygen saturation and temperature effects. One wavelength that is highly absorbing for the blood but far less absorbing to glucose (like 635 nm or 532 nm light) is utilised to eliminate or at least reduce the blood oxygen saturation and temperature effects and another wavelength that is highly absorbing for glucose is used to probe the glucose, which will include the interferences from blood oxygen saturation and temperature as well. As both wavelengths will be affected by SO2 and temperature in a linear manner, a normalisation operation that takes the ratio of the two photo-acoustic signals will eliminate/de-correlate the blood oxygen saturation and temperature effects from glucose measurement.

The feasibility of the technique was explored in an experimental setup. A preliminary measurement of glucose level in a phantom by the proposed PGTS approach was conducted which proves the efficacy of the method. Glucose level in a water tank is linearly increased from 0 to 350 mg/dL by adding glucose solution to it using a syringe pump. The proof of concept measurement is done using single wavelength at 532 nm for glucose measurement. Fixed at the tank bottom is an absorbing target that mimics the vein inside the skin. Based on the relationship of the photo-acoustic signal and glucose concentration explained earlier, the experimental results are shown in FIG. 12. The photo-acoustic method offers a very accurate measurement: it fits with the linear function of actual glucose level with a determination coefficient larger than 0.99. The maximum error of the photo-acoustic measurement in the range from 0 to 300 mg/dL is around 10 mg/dL, close to the results obtained from [12].

Further, a photo-acoustic guided transmission spectroscopy method is disclosed with the capability of measuring glucose accurately in a non-invasive way, which may be repeatable and/or usable for continuous monitoring applications. It may facilitate the diagnosis, treatment and monitoring of diabetes mellitus. In addition, this technique that achieves a virtual photodiode inside tissue may enable sensing with better resolution and higher specificity and it can be extended to measure other molecules for diagnosis of other skin disorders, such as melanoma. Excellent scalability of the photo-acoustic technique and its high-sensitivity on temperature are significant features, and may allow development of a portable temperature monitoring device. The techniques disclosed herein may be used to develop a novel sensor device that can continuously monitor heat strain in a non-invasive way.

It is also to be noted that the above-described blood glucose monitoring technique may be provided separately, for example, in a dedicated sensor apparatus for deriving a de-correlated value of blood glucose of the subject.

Potential Commercial Applications of the Above-Describe Techniques

1. The disclosed photo-acoustic oximeter, based on photo-acoustic sensing, is completely different from current products that used near-infrared spectroscopy (NIRS). Compared to photo-acoustic sensing, NIRS is limited by insufficient sensitivity, volume-averaged inaccuracy due to strong optical scattering and diffusing, poor resolution and consequent inability to measure the SvO2 in high resolution. While the proposed photo-acoustic sensing essentially overcomes all the problems of NIRS, hence it can achieve much better performance than NIRS in terms of resolution, sensitivity and accuracy.

2. As explained previously, the disclosed photo-acoustic oximeter apparatus may use only single wavelength for the measurement of SO2, hence lowering the complexity and cost of the device significantly. It will be comparable and perhaps even lower in price than existing NIRS products.

3. Most oximeter products in the market can only measure SpO2 in finger tips, earlobes, toes, forehead and other parts, which cannot reflect the true delivery and consumption of oxygen by the organ (such as brain) in time; whereas the proposed PA oximeter, besides used as the current products to measure SaO2, can also measure SvO2, which shows the true balance between the delivery and consumption of oxygen by the organs. Currently, the measurement of SvO2 can only be done by inserting the invasive central venous catheters (CVC) into the right atrium of the heart from the internal jugular vein, which is quite inconvenient and only used in ICU.

4. The disclosed PA oximeter solution can concurrently measure multiple core parameters (blood SO2, core temperature, glucose), making the unique solution much more cost effective and robust than existing products.

5. Convenient and reliable temperature monitoring during physical activities, in particular, needs to be made on a non-invasive continuous basis and therefore portable sensors may be necessary which further implicates lightweight and low power consumption for the device. Other applications of the photo-acoustic based temperature measurement method include patient monitoring in hospital intensive care units, as well as monitoring of temperature for incoming people during health crisis situations. This can be integrated into existing hospital care solutions to provide core temperature monitoring.

6. The disclosed PGTS sensor uniquely utilises both optical and acoustic waves. This sensor is capable of measuring glucose accurately in a non-invasive, repeated and continuous manner and will facilitate the diagnosis, treatment and monitoring of diabetes mellitus. In addition, this technique that achieves a virtual photodiode inside tissue enables sensing with better resolution and higher specificity and it can be extended to measure other molecules for diagnosis of other skin disorders, such as melanoma.

7. The PGTS sensor can be readily integrated into a cosmetic laser treatment system, targeting a potentially exploding skincare device market, expected to be worth around U.S. $10.7 billion by 2018.

Overall, the proposed photo-acoustic sensor apparatus may also be configured to measure concurrently multiple parameters (blood oxygen saturation, core temperature and glucose). The approach can de-embed the correlation and interference between different parameters when measuring multiple parameters, therefore making the solution much more cost-effective and robust than existing offerings.

It will be appreciated that the invention has been described by way of example only and that various modifications may be made to the techniques described above without departing from the spirit and scope of the invention.

REFERENCES

[1] L. V. Wang, "Multiscale photoacoustic microscopy and computed tomography," *Nat Photonics*, vol. 3, pp. 503-509, Aug. 29, 2009.

[2] L. V. Wang and S. Hu, "Photoacoustic tomography: in vivo imaging from organelles to organs," *Science*, vol. 335, pp. 1458-62, Mar. 23, 2012.

[3] X. Wang, Y. Pang, G. Ku, X. Xie, G. Stoica, and L. V. Wang, "Noninvasive laser-induced photoacoustic tomography for structural and functional in vivo imaging of the brain," *Nat Biotechnol*, vol. 21, pp. 803-6, July 2003.

[4] R. M. Schell and D. J. Cole, "Cerebral monitoring: Jugular venous oximetry," *Anesthesia and Analgesia*, vol. 90, pp. 559-566, March 2000.

[5] R. V. Kuranov, J. Z. Qiu, A. B. McElroy, A. Estrada, A. Salvaggio, J. Kiel, et al., "Depth-resolved blood oxygen saturation measurement by dual-wavelength photothermal (DWP) optical coherence tomography," *Biomedical Optics Express*, vol. 2, pp. 491-504, Mar. 1, 2011.

[6] L. Gao, L. Wang, C. Li, Y. Liu, H. Ke, C. Zhang, et al., "Single-cell photoacoustic thermometry," *J Biomed Opt*, vol. 18, p. 26003, February 2013.

[7] J. Shah, S. Park, S. Aglyamov, T. Larson, L. Ma, K. Sokolov, et al., "Photoacoustic imaging and temperature measurement for photothermal cancer therapy," *J Biomed Opt*, vol. 13, p. 034024, May-June 2008.

[8] M. Pramanik and L. V. Wang, "Thermoacoustic and photoacoustic sensing of temperature," *J Biomed Opt*, vol. 14, p. 054024, September-October 2009.

[9] S. H. Wang, C. W. Wei, S. H. Jee, and P. C. Li, "Photoacoustic temperature measurements for monitoring of thermal therapy," *Photons Plus Ultrasound: Imaging and Sensing 2009*, vol. 7177, 2009.

[10] P. Zhang, X. Z. Zhang, J. Brown, D. Vistisen, R. Sicree, J. Shaw, et al., "Global healthcare expenditure on diabetes for 2010 and 2030," *Diabetes Research and Clinical Practice*, vol. 87, pp. 293-301, March 2010.

[11] J. T. Oh, M. L. Li, H. F. Zhang, K. Maslov, G. Stoica, and L. H. V. Wang, "Three-dimensional imaging of skin melanoma in vivo by dual-wavelength photoacoustic microscopy," *Journal of Biomedical Optics*, vol. 11, May-June 2006.

[12] M. A. Pleitez, T. Lieblein, A. Bauer, O. Hertzberg, H. von Lilienfeld-Toal, and W. Mantele, "In Vivo Noninvasive Monitoring of Glucose Concentration in Human Epidermis by Mid-Infrared Pulsed Photoacoustic Spectroscopy," *Analytical Chemistry*, vol. 85, pp. 1013-1020, Jan. 15, 2013.

[13] C. W. Freudiger, W. Min, B. G. Saar, S. Lu, G. R. Holtom, C. W. He, et al., "Label-Free Biomedical Imaging with High Sensitivity by Stimulated Raman Scattering Microscopy," *Science*, vol. 322, pp. 1857-1861, Dec. 19, 2008.

[14] R. Filkins, P. Tian, and P. Fomitchov, "System and method for optoacoustic imaging," U.S. Patent 20070015992, Jun. 30, 2005.

[15] M. Igarashi, "Biological observation apparatus and method," U.S. Pat. No. 8,406,847, Jun. 12, 2009.

[16] M. Balberg, R. P. Shechter, and M. Olshansky, "Photoacoustic analyzer of region of interest in a human body," U.S. Pat. No. 7,515,948, Sep. 13, 2004.

[17] D. L. Liu and E. S. Ebbini, "Real-Time 2-D Temperature Imaging Using Ultrasound," *IEEE Transactions on Biomedical Engineering*, vol. 57, pp. 12-16, January 2010.

[18] M. Pernot, M. Tanter, J. Bercoff, K. R. Waters, and M. Fink, "Temperature estimation using ultrasonic spatial compound imaging," *IEEE Transactions on Ultrasonics Ferroelectrics and Frequency Control*, vol. 51, pp. 606-615, May 2004.

[19] L. R. Hirsch, R. J. Stafford, J. A. Bankson, S. R. Sershen, B. Rivera, R. E. Price, et al., "Nanoshell-mediated near-infrared thermal therapy of tumors under magnetic resonance guidance," *Proceedings of the National Academy of Sciences of the United States of America*, vol. 100, pp. 13549-13554, Nov. 11, 2003.

[20] B. Quesson, J. A. de Zwart, and C. T. W. Moonen, "Magnetic resonance temperature imaging for guidance of thermotherapy," *Journal of Magnetic Resonance Imaging*, vol. 12, pp. 525-533, October 2000.

[21] B. Kurt and M. Gulsoy, "Optical and Thermal Response of Laser Irradiated Tissue," *Biyomut: 2009 14th National Biomedical Engineering Meeting*, pp. 406-408, 2009.

[22] P. X. Lai, J. R. McLaughlan, A. B. Draudt, T. W. Murray, R. O. Cleveland, and R. A. Roy, "Real-Time Monitoring of High-Intensity Focused Ultrasound Lesion Formation Using Acousto-Optic Sensing," *Ultrasound in Medicine and Biology*, vol. 37, pp. 239-252, February 2011.

[23] R. Agah, A. H. Gandjbakhche, M. Motamedi, R. Nossal, and R. F. Bonner, "Dynamics of temperature dependent optical properties of tissue: Dependence on thermally induced alteration," *IEEE Transactions on Biomedical Engineering*, vol. 43, pp. 839-846, August 1996.

[24] C. Yu, "Temperature and pressure measuring technique using the photoacoustic effect and mechanical resonance," U.S. Pat. No. 5,085,080, Oct. 5, 1990.

[25] A. Tura, A. Maran, and G. Pacini, "Non-invasive glucose monitoring: Assessment of technologies and devices according to quantitative criteria," *Diabetes Research and Clinical Practice*, vol. 77, pp. 16-40, July 2007.

[26] M.-S. Chou, "Method and apparatus for noninvasive measurement of blood glucose by photoacoustics," U.S. Pat. No. 6,049,728, Nov. 12, 1998.

[27] A. A. Oraevsky and A. A. Karabutov, "Time-resolved optoacoustic method and system for noninvasive monitoring of glucose," U.S. Pat. No. 6,405,069, Oct. 6, 1999.

[28] S. Kanayama, K. Itsumi, O. S. Khalil, and S. Kantor, "Method and apparatus for non-invasive measurement of living body characteristics by photoacoustics," U.S. Pat. No. 8,326,388, Oct. 28, 2003.

[29] G. A. Peyman, "Photoacoustic measurement," U.S. Patent 20120271204, Jun. 28, 2012.

[30] J. Page and J. Plante, "Highly portable and wearable blood analyte measurement system," U.S. Patent 20050054907, Sep. 8, 2003.

[31] H. F. Zhang, K. Maslov, M. Sivaramakrishnan, G. Stoica, and L. H. V. Wang, "Imaging of hemoglobin oxygen saturation variations in single vessels in vivo using photoacoustic microscopy," *Applied Physics Letters*, vol. 90, Jan. 29 2007.

[32] M. H. Xu and L. H. V. Wang, "Photoacoustic imaging in biomedicine," Review of Scientific Instruments, vol. 77, April 2006.

[33] J. K. Chen, M. L. Wang, J. C. Cheng, Y. H. Wang, P. C. Li, and X. Y. Cheng, "A Photoacoustic Imager With Light Illumination Through an Infrared-Transparent Silicon CMUT Array," *IEEE Transactions on Ultrasonics Ferroelectrics and Frequency Control*, vol. 59, pp. 766-775, April 2012.

[34] (2011). Laser safety handbook. Available: http://www.research.northwestern.edu/ors/forms/laser-safety-handbook.pdf

The invention claimed is:

1. A photo-acoustic sensing apparatus for non-invasive measurement of blood parameters of a subject, the photo-acoustic sensing apparatus comprising:

a photo-acoustic sensor for sensing photo-acoustic signals induced when a region of the subject is illuminated by a light source;

a first sensor processor for deriving blood oxygen saturation using the sensed photo-acoustic signals;

a second sensor processor for deriving blood core temperature using the sensed photo-acoustic signals; and a third sensor processor for deriving blood glucose using the sensed photo-acoustic signals; wherein the photo-acoustic sensing apparatus is configured for:

the first sensor processor to derive a de-correlated value of blood oxygen saturation of the subject; and for at least one of:

the second sensor processor to derive a de-correlated value of blood core temperature of the subject; and the third sensor processor to derive a de-correlated value of blood glucose of the subject; the photo-acoustic sensing apparatus further comprising a light sensor for sensing scattered light signals induced when the region of the subject is illuminated by the light source; and wherein the first sensor processor is configured to derive the de-correlated value of blood oxygen saturation of the subject using the sensed photo-acoustic signals and the sensed scattered light signals, the de-correlated value of blood oxygen saturation being related to a ratio of oxygenated haemoglobin in blood of the subject and total haemoglobin in the blood of the subject and being unaffected by variations in the blood core temperature and the blood glucose.

2. The photo-acoustic sensing apparatus of claim 1, configured to derive the de-correlated value of blood oxygen saturation of the subject using a calibration coefficient, molar extinction coefficients of haemoglobin and scattering coefficients.

3. The photo-acoustic sensing apparatus of claim 1, configured to derive the de-correlated value of blood oxygen saturation of the subject using the sensed photo-acoustic signals and the sensed scattered light signals induced when the region of the subject is illuminated by the light source, the light source emitting light of a single wavelength.

4. The photo-acoustic sensing apparatus of claim 1, configured to derive the de-correlated value of the blood oxygen saturation of the subject using the sensed photo-acoustic signals and the sensed scattered light signals induced when the region of the subject is illuminated by the light source, the light source emitting light of a plurality of wavelengths.

5. The photo-acoustic sensing apparatus of claim 1, wherein the second sensor processor is configured:

to derive a first photo-acoustic value when the region of the subject is subjected to illumination by the light source operating in a first signal acquisition mode of operation, and emitting light of an isosbestic wavelength;

to derive a second photo-acoustic value when the region of the subject is subjected to illumination by the light source operating in the first signal acquisition mode of operation, after having been subjected to illumination by the light source operating in a second perturbation mode of operation;

to derive a pressure difference value from the first photo-acoustic value and the second photo-acoustic value;

to derive a normalised second photo-acoustic value using the second photo-acoustic value and the pressure difference value; and to derive the de-correlated value of blood core temperature of the subject using the normalised second photo-acoustic value, a first blood core temperature constant and a second blood core temperature constant.

6. The photo-acoustic sensing apparatus of claim 5, wherein the light source comprises a laser, and the second sensor processor is configured to derive the first blood core temperature constant using:

a first material property constant;
a second material property constant;
a first current value for current supplied to the laser during the first signal acquisition mode of operation;
a second current value for current supplied to the laser during the second perturbation mode of operation;
a laser pulse duration in the first signal acquisition mode of operation;
a duration of the second perturbation mode of operation; and
a heat capacity of haemoglobin.

7. The photo-acoustic sensing apparatus of claim 6, wherein the second sensor processor is configured to derive the second blood core temperature constant using:

the second material property constant;
the first current value for current supplied to the laser during the first signal acquisition mode of operation;
the second current value for current supplied to the laser during the second perturbation mode of operation;
the laser pulse duration in the first signal acquisition mode of operation;
the duration of the second perturbation mode of operation; and
the heat capacity of haemoglobin.

8. The photo-acoustic sensing apparatus of claim 5, wherein the photo-acoustic sensing apparatus is configured to obtain one of the first blood core temperature constant and the second blood core temperature constant during a calibration process.

9. The photo-acoustic sensing apparatus of claim 1, wherein the third sensor processor is configured:

to derive a first glucose photo-acoustic value when the region of the subject is subjected to illumination by the light source emitting light at a first wavelength, the first wavelength being selected for exhibiting a higher absorption in haemoglobin than absorption in glucose;

to derive a second glucose photo-acoustic value when the region of the subject is subjected to illumination by the light source emitting light at a second wavelength, the second wavelength being selected for exhibiting a higher absorption in glucose;

to derive a corrected second glucose photo-acoustic value by normalising the second glucose photo-acoustic value using the first glucose photo-acoustic value; and to derive the de-correlated value of blood glucose of the subject using the corrected second glucose photo-acoustic value.

10. The photo-acoustic sensing apparatus of claim 9, wherein the light source comprises a laser, and the third sensor processor is configured to derive the first glucose photo-acoustic value for blood in a blood vessel of the subject, the first glucose photo-acoustic value being related to:

a laser fluence value for the laser operation at the first wavelength;
a molar absorption coefficient for haemoglobin at the first wavelength;
a total concentration of haemoglobin in the blood;
an absorption coefficient for skin of the patient; and
a distance between a surface of skin of the patient and the blood vessel.

11. The photo-acoustic sensing apparatus of claim 10, wherein the third sensor processor is configured to derive the second glucose photo-acoustic value for blood in the blood vessel of the subject, the second glucose photo-acoustic value being related to:

the total concentration of haemoglobin in the blood;
the absorption coefficient for skin of the patient; and
the distance between the surface of skin of the patient and the blood vessel.

12. A method for non-invasive measurement of blood parameters of a subject, the method comprising:

using a photo-acoustic sensor to sense photo-acoustic signals induced in a region of the subject by illumination from a light source;

using a first sensor processor to derive a de-correlated value of blood oxygen saturation of the subject using the sensed photo-acoustic signals;

using a second sensor processor to derive blood core temperature using the sensed photo-acoustic signals;
using a third sensor processor to derive blood glucose using the sensed photo-acoustic signals; the method further comprising at least one of:
using the second sensor processor to derive a de-correlated value of blood core temperature of the subject; and
using the third sensor processor to derive a de-correlated value of blood glucose of the subject; wherein the method further comprises:
using a light sensor to sense scattered light signals induced in the region of the subject by illumination from the light source; and
deriving the de-correlated value of blood oxygen saturation of the subject using the sensed photo-acoustic signals and the sensed scattered light signals, the de-correlated value of blood oxygen saturation being related to a ratio of oxygenated haemoglobin in blood of the subject and total haemoglobin in the blood of the subject and being unaffected by variations in the blood core temperature and the blood glucose.

* * * * *